United States Patent
McGee et al.

(10) Patent No.: US 6,599,559 B1
(45) Date of Patent: *Jul. 29, 2003

(54) RENEWABLE SURFACE TREATMENT OF SILICONE MEDICAL DEVICES WITH REACTIVE HYDROPHILIC POLYMERS

(75) Inventors: Joseph A. McGee, Rochester, NY (US); Paul L. Valint, Jr., Pittsford, NY (US); James A. Bonafini, Jr., Pittsford, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/541,588

(22) Filed: Apr. 3, 2000

(51) Int. Cl.⁷ .............................. C08J 7/04; G02B 1/12; B05D 5/00; G02C 7/04
(52) U.S. Cl. ...................... 427/2.24; 427/2.1; 427/140; 427/155; 427/164; 427/371; 351/160 H
(58) Field of Search ................. 427/2.1, 162, 164, 427/355, 2.24, 154, 155, 430.1, 444, 140, 371; 351/160 R, 160 M; 510/112–115

(56) References Cited

U.S. PATENT DOCUMENTS

| | | | | |
|---|---|---|---|---|
| 4,734,475 A | * | 3/1988 | Goldenberg et al. | 526/273 |
| 5,177,165 A | * | 1/1993 | Valint, Jr. et al. | 526/245 |
| 5,206,298 A | * | 4/1993 | Kawaguchi | 525/283 |
| 5,219,965 A | * | 6/1993 | Valint, Jr. et al. | 526/245 |
| 5,708,050 A | * | 1/1998 | Nakada et al. | 523/107 |
| 6,008,170 A | * | 12/1999 | Tanaka et al. | 510/114 |

FOREIGN PATENT DOCUMENTS

WO    WO 93/00391    *   1/1993

* cited by examiner

*Primary Examiner*—Shrive P. Beck
*Assistant Examiner*—Wesley Markham
(74) *Attorney, Agent, or Firm*—John E. Thomas

(57) ABSTRACT

The present invention is directed toward the renewable surface treatment of medical devices such as contact lenses and medical implants. In particular, the present invention is directed to a method of modifying the surface of a medical device to increase its biocompatibility or hydrophilicity by coating the device with a removable hydrophilic polymer by means of reaction between reactive functionalities on the hydrophilic polymer which functionalities are complementary to reactive functionalities on or near the surface of the medical device. The present invention is also directed to a contact lens or other medical device having such a surface coating.

17 Claims, 8 Drawing Sheets

FIG. 1 (Control)

FIG. 4 (Control)

RENEWABLE SURFACE TREATMENT OF SILICONE MEDICAL DEVICES WITH REACTIVE HYDROPHILIC POLYMERS

CROSS-REFERENCE TO RELATED APPLICATIONS

This application is related by subject matter to commonly-assigned U.S. application Ser. No. 09/315,620, filed May 20, 1999.

FIELD OF THE INVENTION

The present invention is directed toward the surface treatment of medical devices such as contact lenses and medical implants. In particular, the present invention is directed to a method of renewably modifying the surface of a medical device to increase its biocompatibility or hydrophilicity by coating the device with a hydrophilic polymers by reaction between reactive functionalities in the contact lens material and complementary reactive functionalities on the hydrophilic polymer. The present invention is also directed to a contact lens or other medical device having such a surface coating.

BACKGROUND

Contact lenses made from silicone-containing materials have been investigated for a number of years. Such materials can generally be subdivided into two major classes: hydrogels and non-hydrogels. Non-hydrogels do not absorb appreciable amounts of water, whereas hydrogels can absorb and retain water in an equilibrium state. Hydrogels generally have a water content greater than about five weight percent and more commonly between about 10 to about 80 weight percent. Regardless of their water content, both non-hydrogel and hydrogel silicone contact lenses tend to have relatively hydrophobic, non-wettable surfaces.

Surface structure and composition determine many of the physical properties and ultimate uses of solid materials. Characteristics such as wetting, friction, and adhesion or lubricity are largely influenced by surface characteristics. The alteration of surface characteristics is of special significance in biotechnical applications, where biocompatibility is of particular concern. Therefore, those skilled in the art have long recognized the need for rendering the surface of contact lenses and other medical devices hydrophilic or more hydrophilic. Increasing the hydrophilicity of the contact-lens surface improves the wettability of the contact lenses with tear fluid in the eye. This in turn improves the wear comfort of the contact lenses. In the case of continuous-wear lenses, the surface is especially important. The surface of a continuous-wear lens must be designed not only for comfort, but to avoid adverse reactions such as corneal edema, inflammation, or lymphocyte infiltration. Improved methods have accordingly been sought for modifying the surfaces of contact lenses, particularly high-Dk (highly oxygen permeable) lenses designed for continuous (overnight) wear.

Various patents disclose the attachment of hydrophilic or otherwise biocompatible polymeric chains to the surface of a contact lens in order to render the lens more biocompatible. For example, U.S. Pat. No. 5,652,014 teaches amination of a substrate followed by reaction with other polymers, such as a PEO star molecule or a sulfated polysaccharide. One problem with such an approach is that the polymer chain density is limited due to the difficult of attaching the polymer to the silicone substrate.

U.S. Pat. No. 5,344,701 discloses the attachment of oxazolinone or azlactone monomers to a substrate by means of plasma. The invention has utility in the field of surface-mediated or catalyzed reactions for synthesis or site-specific separations, including affinity separation of biomolecules, diagnostic supports and enzyme membrane reactors. The oxazolinone group is attached to a porous substrate apparently by reaction of the ethylenic unsaturation in the oxazolinone monomer with radicals formed by plasma on the substrate surface. Alternatively, the substrate can be coated with monomers and reacted with plasma to form a cross-linked coating. The oxazolinone groups that have been attached to the surface can then be used to attach a biologically active material, for example, proteins, since the oxazolinone is attacked by amines, thiols, and alcohols. U.S. Pat. No. 5,364,918 to Valint et al. and U.S. Pat. No. 5,352,714 to Lai et al. disclose the use of oxazolinone monomers as internal wetting agents for contact lenses, which agents may migrate to the surface of the contact lens.

U.S. Pat. No. 5,804,318 to Pinchuk et al. discloses lubrifying coatings for reducing the coefficients of friction of surfaces on medical devices, including hydrophilic copolymers containing some monomers having pendant tertiary amine functionality. The hydrogel coatings are covalently bondable to epoxy functionalized surfaces on the medical equipment.

U.S. Pat. No. 4,734,475 to Goldenberg et al. discloses the use of a contact lens fabricated from a polymer comprising oxirane (epoxy) substituted monomeric units in the backbone, such that the outer surfaces of the lens contain a hydrophilic inducing amount of the reaction product of the oxirane monomeric units with a water soluble reactive organic, amine, alcohol, thiol, urea, thiourea, sulfite, bisulfite or thiosulfate.

In view of the above, it would be desirable to find an optically clear, hydrophilic coating for the surface of a silicone medical device that renders the device more biocompatible. It would also be desirable to form a coating for a silicone hydrogel contact lens that is more comfortable for a longer period of time, simultaneously tear-wettable and highly permeable to oxygen. It would be desirable if such a biocompatibilized lens was capable of continuous wear overnight, preferably for a week or more without adverse effects to the cornea. Further, it would be desirable to provide a coating with these properties that can be readily renewed to restore its properties to an as-new state.

SUMMARY OF THE INVENTION

Figure 1:
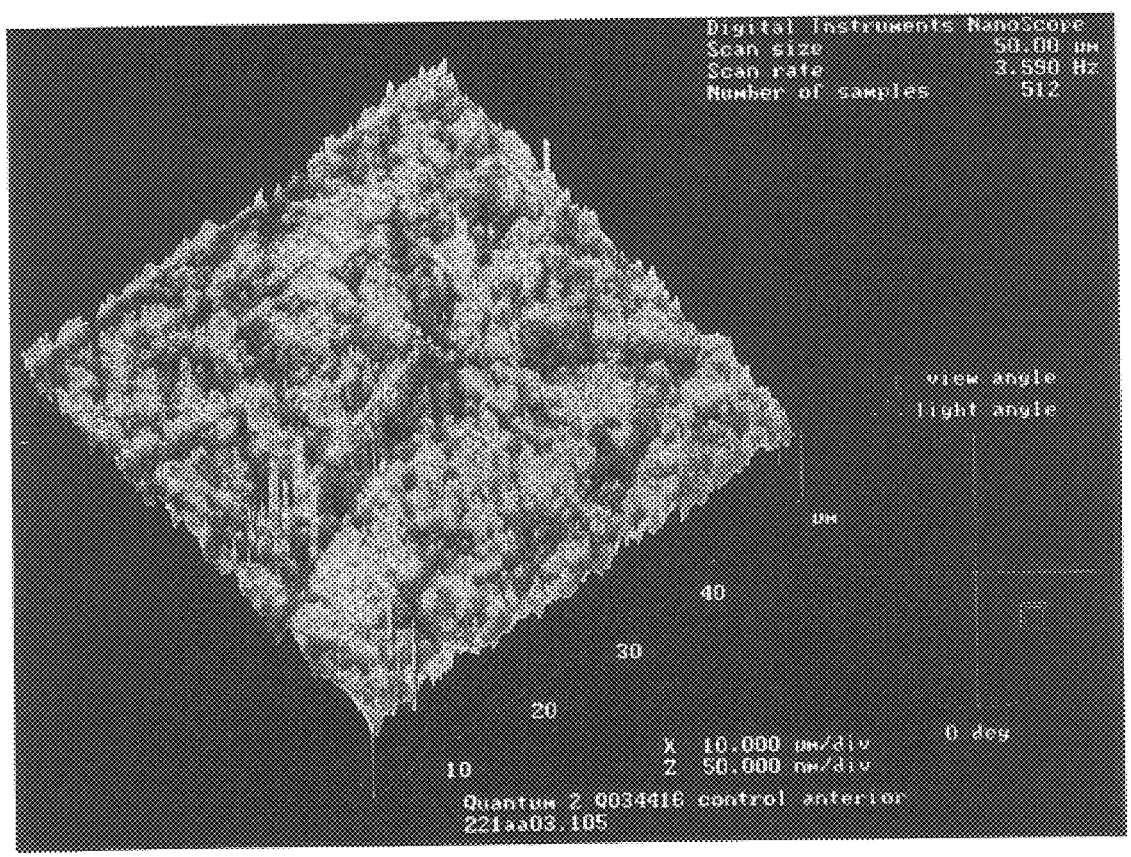
FIG. 1 shows an Atomic Force Microscopy (AFM) topographical image (50 $\mu m^2$) of a control contact lens described in Example 15 below, for comparison to a contact lenses according to the invention; the image of the anterior side of the lens is shown on the left of FIG. 1 and the image of the posterior side is shown on the right.

The present invention is directed toward surface treatment of silicone contact lenses and other silicone medical devices, including a method of modifying the surface of a contact lens to increase its hydrophilicity or wettability. The surface treatment comprises the attachment of hydrophilic polymer chains to the surface of the contact lens substrate by means of reactive functionalities in the lens substrate material reacting with complementary reactive functionalities in monomeric units along a hydrophilic reactive polymer. Subsequently the hydrophilic polymer chains can be removed from the contact lens substrate and then re-applied to achieve substantially as-new surface quality. As used here, the term "as-new surface quality" means a re-applied surface resembling the original surface coating in appearance and material properties.

The present invention is also directed to a medical device, examples of which include contact lenses, intraocular lenses, catheters, implants, and the like, comprising a surface made by such a method.

Examples of medical devices that can be fabricated in accordance with the present invention include dental appliances, including retainers and mouth guards, hearing aids, yams for clothing or for orthopaedic or other medical/surgical implants and appliances such as punctal plugs, stents and braces.

DETAILED DESCRIPTION OF THE INVENTION

As stated above, the present invention is directed toward surface treatment of medical devices, including contact lenses, intraocular lenses and vascular implants, to improve their biocompatibility. The present invention is especially advantageous for application to contact lenses, such as hydrogels, silicone hydrogels, and rigid-gas-permeable lens materials. The invention is especially advantageous for silicone rigid-gas-permeable lenses. Both rigid-gas-permeable ("RGP") materials and hydrogels are well-known classes of materials. By the term silicone, it is meant that the material being treated is an organic polymer comprising at least five percent by weight silicone (—OSi—linkages), preferably 10 to 100 percent by weight silicone, more preferably 30 to 90 percent by weight silicone.

RGP materials typically comprise a hydrophobic cross-linked polymer system containing less than 5 wt. % water. RGP materials useful in accordance with the present invention include those materials taught in U.S. Pat. No. 4,826,936 to Ellis; U.S. Pat. No. 4,463,149 to Ellis; U.S. Pat No. 4,604,479 to Ellis; U.S. Pat. No. 4,686,267 to Ellis et al.; U.S. Pat. No. 4,826,936 to Ellis; U.S. Pat. No. 4,996,275 to Ellis et al.; U.S. Pat. No. 5,032,658 to Baron et al.; U.S. Pat. No. 5,070,215 to Bambury et al.; U.S. Pat. No. 5,177,165 to Valint et al.; U.S. Pat. No. 5,177,168 to Baron et al.; U.S. Pat. No. 5,219,965 to Valint et al.; U.S. Pat. No. 5,336,797 to McGee and Valint; U.S. Pat. No. 5,358,995 to Lai et al.; U.S. Pat. No. 5,364,918 to Valint et al.; U.S. Pat. No. 5,610,252 to Bambury et al.; U.S. Pat. No. 5,708,094 to Lai et al; and U.S. Pat. No. 5,981,669 to Valint et al. U.S. Pat. No. 5,346,976 to Ellis et al. teaches a preferred method of making an RGP material.

Hydrogels comprise hydrated, cross-linked polymeric systems containing water in an equilibrium state. Silicone hydrogels generally have a water content greater than about five weight percent and more commonly between about ten to about eighty weight percent. Such materials are usually prepared by polymerizing a mixture containing at least one silicone-containing monomer and at least one hydrophilic monomer. Either the silicone-containing monomer or the hydrophilic monomer may function as a cross-linking agent (a cross-linker being defined as a monomer having multiple polymerizable functionalities) or a separate cross-linker may be employed. Applicable silicone-containing monomeric units for use in the formation of silicone hydrogels are well known in the art and numerous examples are provided in U.S. Pat. Nos. 4,136,250; 4,153,641; 4,740,533; 5,034,461; 5,070,215; 5,260,000; 5,310,779; and 5,358,995.

Examples of applicable silicon-containing monomeric units include bulky polysiloxanylalkyl (meth)acrylic monomers. An example of bulky polysiloxanylalkyl (meth)acrylic monomers is represented by the following Formula I:

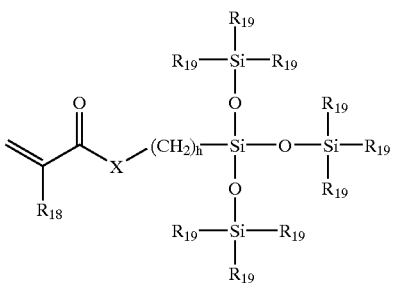 (I)

wherein:
X denotes —O— or —NR—;
each $R_{18}$ independently denotes hydrogen or methyl;
each $R_{19}$ independently denotes a lower alkyl radical, phenyl radical or a group represented by

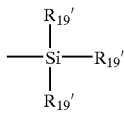

wherein each $R_{19'}$ independently denotes a lower alkyl or phenyl radical; and
h is 1 to 10.

Some preferred bulky monomers are methacryloxypropyl tris(trimethylsiloxy)silane or tris(trimethylsiloxy) silylpropyl methacrylate, sometimes referred to as TRIS and tris(trimethylsiloxy)silylpropyl vinyl carbamate, sometimes referred to as TRIS-VC.

Such bulky monomers may be copolymerized with a silicone macromonomer, which is a poly(organosiloxane) capped with an unsaturated group at two or more ends of the molecule. U.S. Pat. No. 4,153,641 to Deichert et al. discloses, for example, various unsaturated groups, including acryloxy or methacryloxy.

Another class of representative silicone-containing monomers includes silicone-containing vinyl carbonate or vinyl carbamate monomers such as: 1,3-bis[4-vinyloxycarbonyloxy)but-1-yl]tetramethyl-disiloxane; 3-(trimethylsilyl)propyl vinyl carbonate; 3-(vinyloxycarbonylthio)propyl-[tris(trimethylsiloxy) silane]; 3-[tris(trimethylsiloxy)silyl] propyl vinyl carbamate; 3-[tris(trimethylsiloxy)silyl] propyl allyl carbamate; 3-[tris(trimethylsiloxy)silyl]propyl vinyl carbonate; t-butyldimethylsiloxyethyl vinyl carbonate; trimethylsilylethyl vinyl carbonate; and trimethylsilylmethyl vinyl carbonate.

Another class of silicon-containing monomers includes polyurethane-polysiloxane macromonomers (also sometimes referred to as prepolymers), that may have hard-soft-hard blocks like traditional urethane elastomers. Examples of silicone urethanes are disclosed in a variety or publications, including Lai, Yu-Chin, "The Role of Bulky Polysiloxanylalkyl Methacryates in Polyurethane-Polysiloxane Hydrogels," *Journal of Applied Polymer Science*, Vol. 60, 1193–1199 (1996). U.S. Pat. No. 5,760,100, 5,451,617 and 5,451,651 disclose examples of such monomers, which disclosures are hereby incorporated by reference in their entirety. Further examples of silicone urethane monomers are represented by Formulae II and III:

(II) E(*D*A*D*G)$_a$*D*A*D*E'; or (III) E(*D*G*D*A)$_a$*D*G*D*E';

wherein:

D denotes an alkyl diradical, an alkyl cycloalkyl diradical, a cycloalkyl diradical, an aryl diradical or an alkylaryl diradical having 6 to 30 carbon atoms;

G denotes an alkyl diradical, a cycloalkyl diradical, an alkyl cycloalkyl diradical, an aryl diradical or an alkylaryl diradical having 1 to 40 carbon atoms and which may contain ether, thio or amine linkages in the main chain;

* denotes a urethane or ureido linkage;

a is at least 1;

A denotes a divalent polymeric radical of Formula IV:

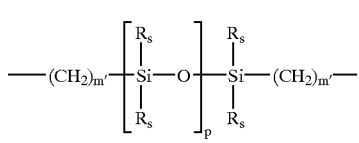 (IV)

wherein:

each Rs independently denotes an alkyl or fluoro-substituted alkyl group having 1 to 10 carbon atoms which may contain ether linkages between carbon atoms;

m' is at least 1; and p is a number that provides a moiety weight of 400 to 10,000;

each of E and E' independently denotes a polymerizable unsaturated organic radical represented by Formula VI:

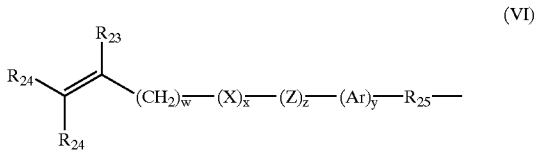 (VI)

wherein:

$R_{23}$ is hydrogen or methyl;

$R_{24}$ is hydrogen, an alkyl radical having 1 to 6 carbon atoms, or a —CO—Y—$R_{26}$ radical wherein Y is —O—, —S— or —NH—;

$R_{25}$ is a divalent alkylene radical having 1 to 10 carbon atoms;

$R_{26}$ is a alkyl radical having 1 to 12 carbon atoms;

X denotes —CO— or —OCO—;

Z denotes —O— or —NH—;

Ar denotes an aromatic radical having 6 to 30 carbon atoms;

w is 0 to 6; x is 0 or 1; y is 0 or 1; and z is 0 or 1.

A preferred silicone-containing urethane monomer is represented by Formula (VII):

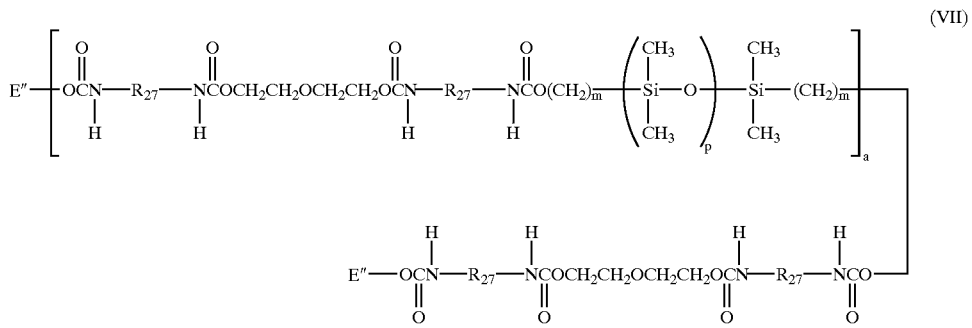

(VII)

wherein m is at least 1 and is preferably 3 or 4, a is at least 1 and preferably is 1, p is a number which provides a moiety weight of 400 to 10,000 and is preferably at least 30, $R_{27}$ is a diradical of a diisocyanate after removal of the isocyanate group, such as the diradical of isophorone diisocyanate, and each E″ is a group represented by:

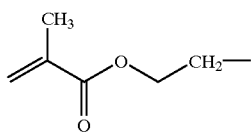

Another class of representative silicone-containing monomers includes fluorinated monomers. Such monomers have been used in the formation of fluorosilicone hydrogels to reduce the accumulation of deposits on contact lenses made therefrom, as described in U.S. Pat. Nos. 4,954,587, 5,079,319 and 5,010,141. The use of silicone-containing monomers having certain fluorinated side groups, i.e. —(CF$_2$)— H, have been found to improve compatibility between the hydrophilic and silicone-containing monomeric units, as described in U.S. Pat. Nos. 5,387,662 and 5,321,108.

In one preferred embodiment of the invention, a silicone hydrogel material comprises (in bulk, that is, in the monomer mixture that is copolymerized) 5 to 50 percent, preferably 10 to 25, by weight of one or more silicone macromonomers, 5 to 75 percent, preferably 30 to 60 percent, by weight of one or more polysiloxanylalkyl (meth) acrylic monomers, and 10 to 50 percent, preferably 20 to 40 percent, by weight of a hydrophilic monomer. Examples of hydrophilic monomers include, but are not limited to, ethylenically unsaturated lactam-containing monomers such as N-vinyl pyrrolidinone, methacrylic and acrylic acids; acrylic substituted alcohols, such as 2-hydroxyethylmethacrylate and 2-hydroxyethylacrylate and acrylamides, such as methacrylamide and N,N-dimethylacrylamide, vinyl carbonate or vinyl carbamate monomers such as disclosed in U.S. Pat. Nos. 5,070,215, and oxazolinone monomers such as disclosed in U.S. Pat. No. 4,910,277. Other hydrophilic monomers such as N,N-dimethyl acrylamide (DMA), 2-hydroxyethyl methacrylate (HEMA), glycerol methacrylate, 2-hydroxyethyl methacrylamide, polyethyleneglycol, monomethacrylate, methacrylic acid and acrylic acid are also useful in the present invention. Other suitable hydrophilic monomers will be apparent to one skilled in the art.

The above silicone materials are merely exemplary, and other materials for use as substrates that can benefit by being coated according to the present invention have been disclosed in various publications and are being continuously developed for use in contact lenses and other medical devices.

As indicated above, the present invention is directed to the modification of the surface of a medical device such as a contact lens by means of removably attaching to the surface hydrophilic polymer chains. The term "removably attaching" refers to creating a chemical bond between the substrate material and the hydrophilic polymer chains which can be severed without substantial mechanical damage to the substrate The hydrophilic polymer chains of the invention can be chemically or mechanically removed from the substrate material, for example by abrasion. Suitable mechanical means include high shear fluidic treatments such as a high speed fluid jet, as well as contacting the surface with a fluidized abrasive solid. The hydrophilic polymeric surface coating may also be mechanically removed by grinding or polishing.

The preferred mechanical method for removing the polymeric surface coating of the invention from contact lenses is rubbing the contact lens with a commercially available abrasive cleaner containing an abrasive such as silica or aluminum oxide together with one or more of an anionic surfactant (such as an alkyl ether sulfonate), a nonionic surfactant (such as an ethoxylated alkyl phenol) and a cationic surfactant (such as a quaternary ammonium salt). Particularly preferred abrasive cleaners include Bostone® and Boston Advanced® brand abrasive cleaners, commercially available from Bausch & Lomb, Rochester, N.Y., 14604.

Suitable chemical means for removing the hydrophilic polymeric surface coating include oxidation, for example oxidative plasma, ozonation or corona discharge. Other chemical means include chemical hydrolysis, hydrolytic cleavage or enzymatic removal.

The hydrophilic polymer chains are attached to the surface by means of exposing the surface to hydrophilic reactive polymers (inclusive of oligomers) having ring-opening or isocyanate reactive functionalities complementary to reactive groups on the surface of the medical device. Alternatively, the hydrophilic polymer chains may be attached to the surface by means of exposing the surface to hydrophilic reactive polymers (inclusive of oligomers) having hydroxy or (primary or secondary) amine groups complementary to azlactone reactive groups in the silicone material or having carboxylic acid complementary groups complementary to epoxy reactive groups in the silicone material. In other words, chemical functionality at the surface of the medical device is utilized to covalently attach hydrophilic polymers to the object or substrate.

The hydrophilic reactive polymers may be homopolymers or copolymers comprising reactive monomeric units that contain either an isocyanate or a ring-opening reactive functionality optionally. Although these reactive monomeric units may also be hydrophilic, the hydrophilic reactive polymer may also be a copolymer of reactive monomeric units copolymerized with one or more of various non-reactive hydrophilic monomeric units. Lesser amounts of hydrophobic monomeric units may optionally be present in the hydrophilic polymer. The ring-opening monomers include azlactone-functional, epoxy-functional and acid-anhydride-functional monomers.

Mixtures of hydrophilic reactive polymers may be employed. For example, the hydrophilic polymer chains attached to the substrate may be the result of the reaction of a mixture of polymers comprising (a) a first hydrophilic reactive polymer having reactive functionalities in monomeric units along the hydrophilic polymers complementary to reactive functionalities on the substrate surface and, in addition, (b) a second hydrophilic reactive polymer having supplemental reactive functionalities that are reactive with the first hydrophilic reactive polymer. A mixture comprising an epoxy-functional polymer with an acid-functional polymer, either simultaneously or sequentially applied to the substrate to be coated, have been found to provide relatively thick coatings. Utilizing a mixture of reactive polymers provides a means to further adjust the surface chemistry of a substrate material.

Preferably the hydrophilic reactive polymers comprise 1 to 100 mole percent of reactive monomeric units, more preferably 5 to 50 mole percent, most preferably 10 to 40 mole percent. The polymers may comprise 0 to 99 mole percent of non-reactive hydrophilic monomeric units, preferably 50 to 95 mole percent, more preferably 60 to 90 mole percent (the reactive monomers, once reacted may also be hydrophilic, but are by definition mutually exclusive with the monomers referred to as hydrophilic monomers which are non-reactive). The weight average molecular weight of the hydrophilic reactive polymer may suitably range from about 200 to 1,000,000, preferably from about 1,000 to 500,000, most preferably from about 5,000 to 100,000.

Hydrophilic monomers may be aprotic types such as acrylamides (N,N-dimethylacrylamide, DMA), lactams such as N-vinylpyrrolidinone, and poly(alkylene oxides) such as methoxypolyoxyethylene methacrylates or may be protic types such as methacrylic acid or hydroxyalkyl (meth) acrylates such as hydroxyethyl (meth)acrylate. Hydrophilic monomers may also include anionic surfactants such as sodium acrylamido-2-methylpropylsulfonate (AMPS) and zwitterions such as N,N-dimethyl-N-methacryloxyethyl-N-(3-sulfopropyl)-ammonium betain (SPE) and N,N-dimethyl-N-methacrylamidopropyl-N-(3-sulfopropyl)-ammonium betain (SPP).

Monomeric units which are hydrophobic optionally may be used in amounts up to 35 mole percent, preferably 0 to 20 mole percent, most preferably 0 to 10 mole percent. Examples of hydrophobic monomers are alkyl methacrylate, fluorinated alkyl methacrylates, long-chain acrylamides such as octyl acrylamide, and the like.

As mentioned above, the hydrophilic reactive polymer may comprise reactive monomeric units derived from azlactone-functional, epoxy-functional and acid-anhydride-functional monomers. For example, an epoxy-functional hydrophilic reactive polymer for coating a lens can be a copolymer containing glycidyl methacrylate (GMA) monomeric units, which will react, for example, with a lens substrate comprising carboxylic acid groups. Preferred examples of anhydride-functional hydrophilic reactive polymers comprise monomeric units derived from monomers such as maleic anhydride and itaconic anhydride.

In general, epoxy-functional reactive groups or anhydride-functional reactive groups in the hydrophilic reactive polymer react with carboxylic (—COOH), alcohol (—OH), primary amine (—NH$_2$) groups or thiol groups (—SH) in the substrate, for example, substrates made from polymers comprising as monomeric units from methacrylic acid (MAA), hydroxyalkylmethacrylates such as hydroxyethylmethacrylate (HEMA), or aminoalkyl methacrylates such as aminopropylmethacrylate, all common and commercially available monomers. In the case of alcohols, a catalyst such as 4-dimethylaminopyridine may be used to speed the reaction at room temperature, as will be understood by the skilled chemist. Acidic groups may also be created in the substrate by the use of azlactone monomeric units that are hydrolyzed to the acid. These acid groups can be reacted with an epoxy or anhydride group in the hydrophilic reactive polymer. See, for example, U.S. Pat. No. 5,364,918 to Valint et al., herein incorporated by reference in its entirety, for examples of such substrates.

In general, azlactone or isocyanate-functional groups in the hydrophilic reactive polymers may similarly react with amines or alcohols in the polymer substrate, reactions involving an alcohol preferably in the presence of a catalyst. In addition, carboxylic acids, amines and hydrolyzed azlactones in the hydrophilic reactive polymers may react with epoxy-groups in the substrate, for example, the monomeric units described in U.S. Pat. No. 4,734,475 to Goldenberg et al., herein incorporated by reference in its entirety.

In a preferred embodiment of the invention, preformed (non-polymerizable) hydrophilic polymers containing repeat units derived from at least one ring-opening monomer, an isocyanate-containing monomer, an amine-containing monomer, a hydroxy-containing monomer, or a carboxylic containing monomer are reacted with reactive groups on the surface of the medical device such as a contact lens substrate. Typically, the hydrophilic reactive polymers are attached to the substrate at one or more places along the chain of the polymer. After attachment, any unreacted reactive functionalities in the hydrophilic reactive polymer may be hydrolyzed to a non-reactive moiety, in the case of epoxy, isocyanate or ring-opening monomeric units.

Suitable hydrophilic non-reactive monomers for comprising the hydrophilic reactive polymers include generally water soluble conventional vinyl monomers such as 2-hydroxyethyl-; 2- and 3-hydroxypropyl-; 2,3-dihydroxypropyl-; polyethoxyethyl-; and polyethoxypropylacrylates, methacrylates, acrylamides and methacrylamides; acrylamide, methacrylamide, N-methylacrylamide, N-methylmethacrylamide, N,N-dimethylacrylamide, N,N-dimethylmethacrylamide, N,N-dimethyl- and N,N-diethyl-aminoethyl acrylate and methacrylate and the corresponding acrylamides and methacrylamides; 2- and 4-vinylpyridine; 4- and 2-methyl-5-vinylpyridine; N-methyl-4-vinylpiperidine; 2-methyl-1-vinylimidazole; N,-N-dimethylallylamine; dimethylaminoethyl vinyl ether and N-vinylpyrrolidone.

Included among the useful non-reactive monomers are generally water soluble conventional vinyl monomers such as acrylates and methacrylates of the general structure

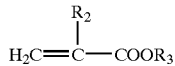

where $R_2$ is hydrogen or methyl and $R_3$ is hydrogen or is an aliphatic hydrocarbon group of up to 10 carbon atoms substituted by one or more water solubilizing groups such as carboxy, hydroxy, amino, lower alkylamino, lower dialkyamino, a polyethylene oxide group with from 2 to about 100 repeating units, or substituted by one or more sulfate, phosphate, sulfonate, phosphonate, carboxamido, sulfonamido or phosphonamido groups, or mixtures thereof;

Preferably $R_3$ is an oligomer or polymer such as polyethylene glycol, polypropylene glycol, poly(ethylene-propylene) glycol, poly(hydroxyethyl methacrylate), poly(dimethyl acrylamide), poly(acrylic acid), poly(methacrylic acid), polysulfone, poly(vinyl alcohol), polyacrylamide, poly(acrylamide-acrylic acid) poly(styrene sulfonate) sodium salt, poly(ethylene oxide), poly(ethylene oxide-propylene oxide), poly(glycolic acid), poly(lactic acid), poly(vinylpyrrolidone), cellulosics, polysaccharides, mixtures thereof, and copolymers thereof;

acrylamides and methacrylamides of the formula:

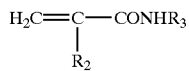

where $R_2$ and $R_3$ are as defined above;
acrylamides and methacrylamides of the formula:

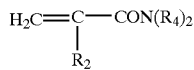

where $R_4$ is lower alkyl of 1 to 3 carbon atoms and $R_2$ is as defined above;
itaconates of the formula:

where $R_3$ is as defined above;
maleates and fumarates of the formula:

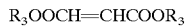

wherein $R_3$ is as defined above;
vinyl ethers of the formula

where $R_3$ is as defined above;
aliphatic vinyl compounds of the formula

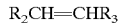

where $R_2$ is as defined above and $R_3$ is as defined above with the proviso that $R_3$ is other than hydrogen; and
vinyl substituted heterocycles, such as vinyl pyridines, piperidines and imidazoles and N-vinyl lactams, such as N-vinyl-2-pyrrolidone.

Included among the useful water soluble monomers are acrylic and methacrylic acid; itaconic, crotonic, fumaric and maleic acids and the lower hydroxyalkyl mono and diesters thereof, such as the 2-hydroxethyl fumarate and maleate, sodium acrylate and methacrylate; 2-methacryloyloxyethylsulfonic acid and allylsulfonic acid.

The inclusion of some hydrophobic monomers in the hydrophilic reactive polymers may provide the benefit of causing the formation of tiny dispersed polymer aggregates in solution, evidenced by a haziness in the solution of the polymer. Such aggregates can also be observed in Atomic Force Microscopy images of the coated medical device.

Suitable hydrophobic copolymerizable monomers include water insoluble conventional vinyl monomers such as acrylates and methacrylates of the general formnula:

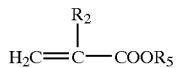

where $R_2$ is as defined above and $R_5$ is a straight chain or branched aliphatic, cycloaliphatic or aromatic group having up to 20 carbon atoms which is unsubstituted or substituted by one or more alkoxy, alkanoyloxy or alkyl of up to 12 carbon atoms, or by halo, especially chloro or preferably fluoro, C2 to C5 polyalkyleneoxy of 2 to about 100 units or an oligomer such as polyethylene, poly(methyl methacrylate), poly(ethyl methacrylate), or poly(glycidyl methacrylate), mixtures thereof, and copolymers thereof;

acrylamides and methacylamides of the general formula:

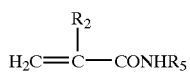

where $R_2$ and $R_5$ are defined above;
vinyl ethers of the formula

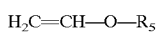

where $R_5$ is as defined above;
vinyl esters of the formula

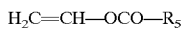

where $R_5$ is as defined above;
itaconates of the formula:

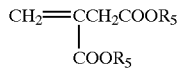

where $R_5$ is as defined above;
maleates and fumarates of the formula

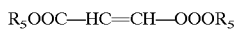

where $R_5$ is as defined above; and
vinylic substituted hydrocarbons of the formula:

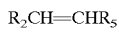

where $R_2$ and $R_5$ is as defined above

Useful or suitable hydrophobic monomers include, for example: methyl, ethyl, propyl, isopropyl, butyl, ethoxyethyl, methoxyethyl, ethoxypropyl, phenyl, benzyl, cyclohexyl, hexafluoroisopropyl, or n-octyl-acrylates and—methacrylates as well as the corresponding acrylamides and methacrylamides; dimethyl fumarate, dimethyl itaconate, dimethyl maleate, diethyl fumarate, methyl vinyl ether, ethoxyethyl vinyl ether, vinyl acetate, vinyl propionate, vinyl benzoate, acrylonitrile, styrene, alpha-methylstyrene, 1-hexene, vinyl chloride, vinyl methylketone, vinyl stearate, 2-hexene and 2-ethylhexyl methacrylate.

The hydrophilic reactive polymers are synthesized in a manner known per se from the corresponding monomers (the term monomer here also including a macromer) by a polymerization reaction customary to the person skilled in the art. Typically, the hydrophilic reactive polymers or chains are formed by: (1) mixing the monomers together; (2)

adding a polymerization initiator; (3) subjecting the monomer/initiator mixture to a source of ultraviolet or actinic radiation and/or elevated temperature and curing said mixture. Typical polymerization initiators include free-radical-generating polymerization initiators of the type illustrated by acetyl peroxide, lauroyl peroxide, decanoyl peroxide, coprylyl peroxide, benzoyl peroxide, tertiary butyl peroxypivalate, sodium percarbonate, tertiary butyl peroctoate, and azobis-isobutyronitrile (AIBN). Ultraviolet free-radical initiators illustrated by diethoxyacetophenone can also be used. The curing process will of course depend upon the initiator used and the physical characteristics of the comonomer mixture such as viscosity. In any event, the level of initiator employed will vary within the range of 0.001 to 2 weight percent of the mixture of monomers. Usually, a mixture of the above-mentioned monomers is warmed with addition of a free-radical former.

A polymerization to form the hydrophilic reactive polymer can be carried out in the presence or absence of a solvent. Suitable solvents are in principle all solvents which dissolve the monomer used, for example water; alcohols such as lower alkanols, for example, ethanol and methanol; carboxamides such as dimethylformamide, dipolar aprotic solvents such as dimethyl sulfoxide or methyl ethyl ketone; ketones such as acetone or cyclohexanone; hydrocarbons such as toluene; ethers such as THF, dimethoxyethane or dioxane; halogenated hydrocarbons such as trichloroethane, and also mixtures of suitable solvents, for example mixtures of water and an alcohol, for example a water/ethanol or water/methanol mixture.

In a method according to the present invention, the contact lens or other medical device may be exposed to hydrophilic reactive polymers by immersing the substrate in a solution containing the polymers. For example, a contact lens may be placed or dipped for a suitable period of time in a solution of the hydrophilic reactive polymer or copolymer in a suitable medium, for example, an aprotic solvent such as acetonitrile.

As indicated above, one embodiment of the invention involves the attachment of reactive hydrophilic polymers to a medical device, which polymers comprise isocyanate-containing monomeric units or ring-opening monomeric units. In one embodiment of the present invention, the ring-opening reactive monomer has an azlactone group represented by the following formula:

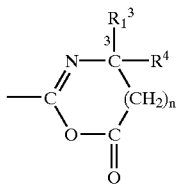

wherein $R^3$ and $R^4$ independently can be an alkyl group having 1 to 14 carbon atoms, a cycloalkyl group having 3 to 14 carbon atoms, an aryl group having 5 to 12 ring atoms, an arenyl group having 6 to 26 carbon atoms, and 0 to 3 heteroatoms non-peroxidic selected from S, N, and O, or $R^3$ and $R^4$ taken together with the carbon to which they are joined can form a carbocyclic ring containing 4 to 12 ring atoms, and n is an integer 0 or 1. Such monomeric units are disclosed in U.S. Pat. No. 5,177,165 to Valint et al.

The ring structure of such reactive functionalities is susceptible to nucleophilic ring-opening reactions with complementary reactive functional groups on the surface of the substrate being treated. For example, the azlactone functionality can react with primary amines, hydroxyls, or thiols in the substrate, as mentioned above, to form a covalent bond between the substrate and the hydrophilic reactive polymer at one or more locations along the polymer. A plurality of attachments can form a series of polymer loops on the substrate, wherein each loop comprises a hydrophilic chain attached at both ends to the substrate.

Azlactone-functional monomers for making the hydrophilic reactive polymer can be any monomer, prepolymer, or oligomer comprising an azlactone functionality of the above formula in combination with a vinylic group on an unsaturated hydrocarbon to which the azlactone is attached. Preferably, azlactone-functionality is provided in the hydrophilic polymer by 2-alkenyl azlactone monomers. The 2-alkenyl azlactone monomers are known compounds, their synthesis being described, for example, in U.S. Pat. Nos. 4,304,705; 5,081,197; and 5,091,489 (all Heilmann et al.) the disclosures of which are incorporated herein by reference. Suitable 2-alkenyl azlactones include:

2-ethenyl-1,3-oxazolin-5-one,
2-ethenyl-4-methyl-1,3-oxazolin-5-one,
2-isopropenyl-1,3-oxazolin-5-one,
2-isopropenyl-4-methyl-1,3-oxazolin-5-one,
2-ethenyl-4,4-dimethyl-1,3-oxazolin-5-one,
2-isopropenyl-4,-dimethyl-1,3-oxazolin-5-one,
2-ethenyl-4-methyl-ethyl-1,3-oxazolin-5-one,
2-isopropenyl-4-methyl-4-butyl-1,3-oxazolin-5-one,
2-ethenyl-4,4-dibutyl-1,3-oxazolin-5-one,
2-isopropenyl-4-methyl-4-dodecyl-1,3-oxazolin-5-one,
2-isopropenyl-4,4-diphenyl-1,3-oxazolin-5-one,
2-isopropenyl-4,4-pentamethylene-1,3-oxazolin-5-one,
2-isopropenyl-4,4-tetramethylene-1,3-oxazolin-5-one,
2-ethenyl-4,4-diethyl-1,3-oxazolin-5-one,
2-ethenyl-4-methyl-4-nonyl-1,3-oxazolin-5-one,
2-isopropenyl-methyl-4-phenyl-1,3-oxazolin-5-one,
2-isopropenyl-4-methyl-4-benzyl-1,3-oxazolin-5-one, and
2-ethenyl-4,4-pentamethylene-1,3-oxazolin-5-one, More preferably, the azlactone monomers are a compound represented by the

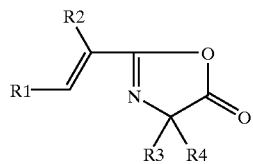

following general formula:

where $R^1$ and $R^2$ independently denote a hydrogen atom or a lower alkyl radical with one to six carbon atoms, and $R^3$ and $R^4$ independently denote alkyl radicals with one to six carbon atoms or a cycloalkyl radical with five or six carbon atoms. Specific examples include 2-isopropenyl-4,4-dimethyl-2-oxazolin-5-one (IPDMO), 2-vinyl-4,4-dimethyl-2-oxazolin-5-one (VDMO), spiro-4'-(2'-isopropenyl-2'-oxazolin-5-one) cyclohexane (IPCO), cyclohexane-spiro-4'-(2'-vinyl-2'-oxazol-5'-one) (VCO), and 2-(-1-propenyl)-4,4-dimethyl-oxazol-5-one (PDMO) and the like.

These compounds may be prepared by the general reaction sequence:

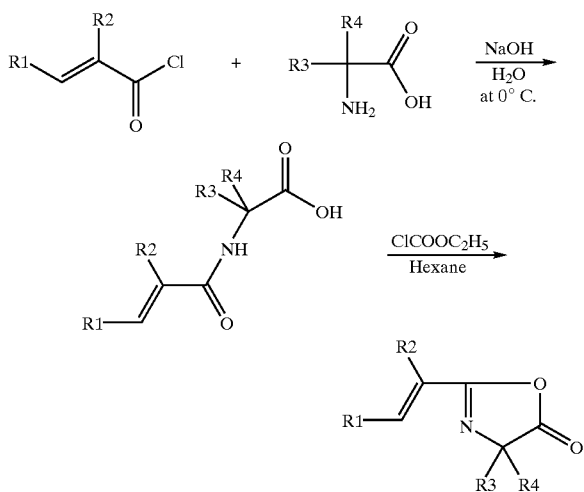

The first step is a Shotten-Bauman acylation of an amino acid. The polymerizable functionality is introduced by using either acryloyl or methacryloyl chloride. The second step involves a ring closure with a chloroformate to yield the desired oxazolinone. The product is isolated and purified by the usual procedures of organic chemistry.

As indicated above, the compounds can be copolymerized with hydrophilic and/or hydrophobic comonomers to form hydrophilic reactive polymers. After attachment to the desired substrate, any unreacted oxazolinone groups may then be hydrolyzed in order to convert the oxazolinone components into amino acids. In general, the hydrolysis step will follow the general reaction of:

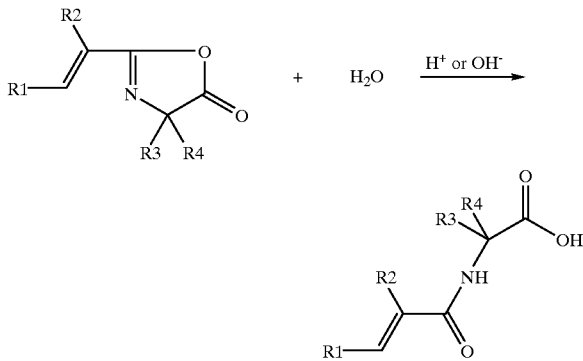

The carbon-carbon double bond between the $R^1$ and $R^2$ radicals is shown unreacted, but the reaction can take place when copolymerized into a polymer.

Non-limiting examples of comonomers useful to be copolymerized with azlactone functional moieties to form the hydrophilic reactive polymers used to coat a medical device include those mentioned above, preferably dimethylacrylamide, N-vinyl pyrrolidinone. Further examples of comonomers are disclosed in European Pat. Publication 0 392 735, the disclosure of which is incorporated by reference. Preferably, dimethylacrylamide is used as a comonomer in order to impart hydrophilicity to the copolymer.

Such azlactone-functional monomers can be copolymerized with other monomers in various combinations of weight percentages. Using a monomer of similar reactivity ratio to that of an azlactone monomer will result in a random copolymer. Determnination of reactivity ratios for copolymerization are disclosed in Odian, *Principles of Polymerization*, 2nd Ed., John Wiley & Sons, p. 425–430 (1981), the disclosure of which is incorporated by reference herein. Alternatively, use of a comonomer having a higher reactivity to that of an azlactone will tend to result in a block copolymer chain with a higher concentration of azlactone-functionality near the terminus of the chain.

Although not as preferred as monomers, azlactone-functional prepolymers or oligomers having at least one free-radically polymerizable site can also be utilized for providing azlactone-functionality in the hydrophilic reactive polymer according to the present invention. Azlactone-functional oligomers, for example, are prepared by free radical polymerization of azlactone monomers, optionally with comonomers as described in U.S. Pat. Nos. 4,378,411 and 4,695,608, incorporated by reference herein. Non-limiting examples of azlactone-functional oligomers and prepolymers are disclosed in U.S. Pat. Nos. 4,485,236, 5,081,197 and 5,292,840, all incorporated by reference herein.

In another embodiment of the invention, the ring-opening reactive group in the hydrophilic reactive polymer is an epoxy functionality. The preferred epoxy-functional monomer is an oxirane-containing monomer such as glycidyl methacrylate, allyl glycidyl ether, 4-vinyl-1-cyclohexene-1, 2-epoxide and the like, although other epoxy-containing monomers may be used.

The hydrophilic reactive polymers are attached to medical devices which may be made by conventional manufacturing processes. For example, contact lenses for application of the present invention can be manufactured employing various conventional techniques, to yield a shaped article having the desired posterior and anterior lens surfaces. Spincasting methods are disclosed in U.S. Pat. Nos. 3,408,429 and 3,660,545; preferred static casting methods are disclosed in U.S. Pat. Nos. 4,113,224 and 4,197,266. Curing of the monomeric mixture is often followed by a machining operation in order to provide a contact lens having a desired final configuration. As an example, U.S. Pat. No. 4,555,732 discloses a process in which an excess of a monomeric mixture is cured by spincasting in a mold to form a shaped article having an anterior lens surface and a relatively large thickness. The posterior surface of the cured spincast article is subsequently lathe cut to provide a contact lens having the desired thickness and posterior lens surface. Further machining operations may follow the lathe cutting of the lens surface, for example, edge-finishing operations.

After producing a lens having the desired final shape, it is desirable to remove residual solvent from the lens before edge-finishing operations. This is because, typically, an organic diluent is included in the initial monomeric mixture in order to minimize phase separation of polymerized products produced by polymerization of the monomeric mixture and to lower the glass transition temperature of the reacting polymeric mixture, which allows for a more efficient curing process and ultimately results in a more uniformly polymerized product. Sufficient uniformity of the initial monomeric mixture and the polymerized product are of particular concern for silicone hydrogels, primarily due to the inclusion of silicone-containing monomers which may tend to separate from the hydrophilic comonomer. Suitable organic diluents include, for example, 2-hydoxy, 2-methyl decane, monohydric alcohols, with $C_6$–$C_{10}$ straight-chained or branched alcohols including aliphatic monohydric alcohols such as n-hexanol and n-nonanol being especially preferred. U.S. Pat. No. 6,020,445 to Vanderlaan et al. discloses suitable alcohols and is incorporated herein by reference. Other useful solvents include diols such as ethylene glycol; polyols such as glycerin; ethers such as diethylene glycol monoethyl ether; ketones such as methyl ethyl ketone; esters such as methyl enanthate; and hydrocarbons such as toluene. Preferably, the organic diluent is sufficiently volatile to facilitate its removal from a cured article by evaporation at or near ambient pressure. Generally, the diluent is included at five to sixty percent by weight of the monomeric mixture, with ten to fifty percent by weight being especially preferred.

The cured lens is then subjected to solvent removal, which can be accomplished by evaporation at or near ambient pressure or under vacuum. An elevated temperature can be employed to shorten the time necessary to evaporate the diluent. The time, temperature and pressure conditions for the solvent removal step will vary depending on such factors as the volatility of the diluent and the specific monomeric components, as can be readily determined by one skilled in the art. According to a preferred embodiment, the temperature employed in the removal step is preferably at least 50° C., for example, 60 to 80° C. A series of heating cycles in a linear oven under inert gas or vacuum may be used to optimize the efficiency of the solvent removal. The cured article after the diluent removal step should contain no more than twenty percent by weight of diluent, preferably no more than five percent by weight or less.

Following removal of the organic diluent, the lens is next subjected to mold release and optional machining operations. The machining step includes, for example, buffing or polishing a lens edge and/or surface. Generally, such machining processes may be performed before or after the article is released from a mold part. Preferably, the lens is dry released from the mold by employing vacuum tweezers to lift the lens from the mold, after which the lens is transferred by means of mechanical tweezers to a second set of vacuum tweezers and placed against a rotating surface to smooth the surface or edges. The lens may then be turned over in order to machine the other side of the lens.

Subsequent to the mold release/machining operations, the lens is subjected to surface treatment according to the present invention, as described above, including the attachment of the hydrophilic reactive polymer chains.

Subsequent to the step of surface treatment, the lens may be subjected to extraction to remove residuals in the lenses. Generally, in the manufacture of contact lenses, some of the monomer mix is not fully polymerized. The incompletely polymerized material from the polymerization process may affect optical clarity or may be harmful to the eye. Residual material may include solvents not entirely removed by the previous solvent removal operation, unreacted monomers from the monomeric mixture, oligomers present as by-products from the polymerization process, or even additives that may have migrated from the mold used to form the lens.

Conventional methods to extract such residual materials from the polymerized contact lens material include extraction with an alcohol solution for several hours (for extraction of hydrophobic residual material) followed by extraction with water (for extraction of hydrophilic residual material). Thus, some of the alcohol extraction solution remains in the polymeric network of the polymerized contact lens material, and should be extracted from the lens material before the lens may be worn safely and comfortably on the eye. Extraction of the alcohol from the lens can be achieved by employing heated water for several hours. Extraction should be as complete as possible, since incomplete extraction of residual material from lenses may contribute adversely to the useful life of the lens. Also, such residuals may impact lens performance and comfort by interfering with optical clarity or the desired uniform hydrophilicity of the lens surface. It is important that the selected extraction solution in no way adversely affects the optical clarity of the lens. Optical clarity is subjectively understood to be the level of clarity observed when the lens is visually inspected.

Subsequent to extraction, the lens is subjected to hydration in which the lens is fully hydrated with water, buffered saline, or the like. When the lens is ultimately fully hydrated (wherein the lens typically may expand by 10 to about 20 percent or more), the coating remains intact and bound to the lens, providing a durable, hydrophilic coating which has been found to be resistant to delamination.

Following hydration, the lens may undergo cosmetic inspection wherein trained inspectors inspect the contact lenses for clarity and the absence of defects such as holes, particles, bubbles, nicks, tears. Inspection is preferably at 10×magnification. After the lens has passed the steps of cosmetic inspection, the lens is ready for packaging, whether in a vial, plastic blister package, or other container for maintaining the lens in a sterile condition for the consumer. Finally, the packaged lens is subjected to sterilization, which sterilization may be accomplished in a conventional autoclave, preferably under an air pressurization sterilization cycle, sometimes referred to as an air-steam mixture cycle, as will be appreciated by the skilled artisan. Preferably the autoclaving is at 100° C. to 200° C. for a period of 10 to 120 minutes. Following sterilization, the lens dimension of the sterilized lenses may be checked prior to storage.

Examples of rigid-gas-permeable ("RGP") materials useful in the present invention include the materials prepared from silicone-containing monomers as taught in U.S. Pat. Nos. 4,152,508; 4,330,383; 4,686,267; 4,826,889; 4,826,936; 4,861,850; 4,996,275; and 5,346,976. The teachings of these patents are expressly incorporated herein by reference. The RGP materials do not generally require solvent removal or extraction steps before they are used as substrates in accordance with the invention.

Objects and advantages of this invention are further illustrated by the following examples, but the particular materials and amounts thereof recited in these examples, as well as other conditions and details should not be construed at unduly limit this invention.

EXAMPLE 1

This example discloses a representative silicone hydrogel lens material used as a coating substrate in the following Examples. The formulation for the material is provided in Table 1 below.

TABLE 1

| Component | Parts by Weight |
|---|---|
| TRIS-VC | 55 |
| NVP | 30 |
| $V_2D_{25}$ | 15 |
| VINAL | 1 |
| n-nonanol | 15 |
| Darocur | 0.2 |
| tint agent | 0.05 |

The following materials are designated above:

| | |
|---|---|
| TRIS-VC | tris(trimethylsiloxy)silylpropyl vinyl carbamate |
| NVP | N-vinyl pyrrolidone |
| $V_2D_{25}$ | a silicone-containing vinyl carbonate as previously described in U.S. Pat. No. 5,534,604. |
| VINAL | N-vinyloxycarbonyl alanine |
| Darocur | Darocur-1173, a UV initiator |
| tint agent | 1,4-bis[4-(2-methacryloxyethyl)phenylamino] anthraquinone |

EXAMPLE 2

This Example illustrates a process for preparation of a contact lens prior to surface modification of a contact lens according to the present invention. Silicone hydrogel lenses made of the formulation of Example 1 above were cast-molded from polypropylene molds. Under an inert nitrogen atmosphere, 45-μl of the formulation was injected onto a clean polypropylene concave mold half and covered with the complementary polypropylene convex mold half. The mold halves were compressed at a pressure of 70 psi and the mixture was cured for about 15 minutes in the presence of UV light (6–11 mW/cm² as measured by a Spectronic UV meter). The mold was exposed to UV light for about 5 additional minutes. The top mold half was removed, and the lenses were maintained at 60° C. for 3 hours in a forced air oven to remove n-nonanol. Subsequently, the lens edges were ball buffed for 10 seconds at 2300 rpm with a force of 60 g.

EXAMPLE 3

This example illustrates the synthesis of the hydrophilic reactive copolymer involving a 80/20 by weight percent ratio of monomers (DMA/VDMO) employing the ingredients in Table 2 below:

TABLE 2

| Reagents | Amount (g) | Amount (m) |
|---|---|---|
| Dimethylacrylamide (DMA) | 16 g | 0.1614 |
| Vinyl-4,4-dimethyl-2-oxazolin-5-one (VDMO) | 4 g | 0.0288 |
| VAZO-64 initiator | 0.031 g | 0.1 percent |
| Toluene | 200 ml | — |

All ingredients except VAZO-64 were placed in a 500-ml round-bottom flask equipped with a magnetic stirrer, condenser, argon blanket, and thermo-controller. The above was de-aerated with argon for 30 min. After VAZO-64 was added, the solution was heated to 60° C. and maintained for 50 hrs. After the reaction was complete as monitored by FTIR (Fourier Transform Infrared spectroscopy), the solution was slowly added to 2500 ml of diethyl ether to precipitate the polymer. The mixture was stirred 10 min, allowed to settle 10 min, and filtered. The precipitate was dried under vacuum at 30 to 35° C. overnight, and the molecular weight determined to be Mn=19448, Mw=43548 and Pd=2.25, all based on polystyrene standards. (Pd refers to polydispersity.)

EXAMPLE 4

This Example illustrates the synthesis of a prepolymer of N,N-dimethylacrylamide that is used in making a macromonomer (or "acromer") for eventual use in a reactive hydrophilic polymer according to the present invention. The prepolymer is made according to the following reaction scheme.

Reagents DMA (200 g, 2.0 moles), mercaptoethanol (3.2 g, 0.041 moles), AIBN (Vazo-64 in the amount 3.3 g, 0.02 moles) and tetrahydrofuran (1,000 ml) were combined in a two liter round bottom flask fitted with a magnetic stirrer, condenser, thermal controller and a nitrogen inlet. Nitrogen gas was bubbled through the solution for one half-hour. The temperature was increased to 60° C. for 72 hours under a passive blanket of nitrogen. The polymer was precipitated from the reaction mixture with 20 liters of ethyl ether (171.4 g of polymer was isolated). A sample submitted for SEC (size exclusion chromatography) analysis gave a Mn=3711, Mw=7493, and Pd=2.02.

EXAMPLE 5

This Example illustrates the synthesis of a macromer of DMA using the prepolymer of Example 4 which macromonomer is used to make the hydrophilic reactive polymer of Examples 6 and 8 below, which macromonomer is made according to the following reaction scheme:

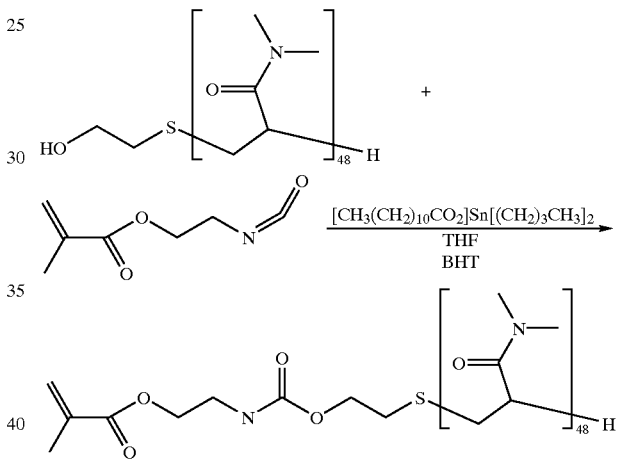

The prepolymer from Example 4 (150 g, 0.03 moles), isocyanatoethylmethacrylate (IEM, 5.6 g, 0.036 moles), dibutyltindilaurate (0.23 g, 3.6×10⁻⁵ moles), tetrahydrofuran (THF, 1000 ml) and 2,6-di-tert-butyl-4-methyl phenol (BHT, 0.002 g, 9×10⁻⁶ moles) were combined under a nitrogen blanket. The mixture was heated to 35° C. with good stirring for seven hours. Heating was stopped, and the mixture was allowed to stir under nitrogen overnight. Several ml of methanol were added to react with any remaining IEM. The macromonomer was then collected after precipitation from a large volume (16 liters) of ethyl ether. The solid was dried under house vacuum (yield 115 g). Size exclusion chromatography of the polymer verses polystyrene standards gave the following results: Mn=2249, Mw=2994, and Pd=1.33.

EXAMPLE 6

This Example illustrates the preparation of a DMA/DMA-mac/VDMO polymer which may be used to form a coating according to the present invention. Dimethylacrylamide (DMA) in the amount of 16 g (0.1614 mole), vinyl-4,4-dimethyl-2-oxazolin-5-one (VDMO) in the amount of 2 g (0.0144 mole), dimethylacrylamide macromer (DMA-mac) as prepared in Example 5, in the amount of 2 g (0.0004 mole), and 200 ml of toluene were placed in a 500-ml round-bottom flask equipped with a magnetic stirrer, condenser, argon blanket, and temperature controller. The solution was de-aerated with argon for 30 min. Then 0.029 g (0.1 mole %) of VAZO-64 was added and the reaction heated to 60° C. for 50 hrs. After the reaction was complete (monitored by FTIR), the solution was slowly added to 2500 ml of ethyl ether to precipitate the polymer. After the addition was complete, the mixture was stirred 10 min, allowed to settle 10 min, and filtered. The precipitate was dried under house vacuum at 30 to 35° C. overnight. The dried polymer was sampled for analysis by gel permeation chromatography, bottled and stored in a desiccator.

EXAMPLE 7

This Example illustrates the preparation of a DMA/PEOMA/VDMO polymer usable to coat a silicone substrate according to the present invention. Dimethylacrylamide, in the amount of 12 g (0.1211 mole), vinyl-4,4-dimethyl-2-oxazolin-5-one in the amount of 4 g (0.0288 mole), and 4 g (0.0036 mole) PEO methacrylate (PEOMA), which monomer has a MW of 1000, and 200 ml of toluene were placed in a 500 ml round-bottom flask equipped with a magnetic stirrer, condenser, argon blanket, and temperature controller. The solution was de-aerated with argon for 30 min. Then 0.025 g (0.1 mole %) of VAZO-64 was added, and the reaction heated to 60° C. for 50 hrs. After the reaction was complete (monitored by FTIR), the solution was slowly added to 2500 ml of ethyl ether to the polymer. After the addition was complete, the mixture was stirred 10 min, allowed to settle 10 min, and filtered. The precipitate was dried under house vacuum at 30 to 35° C. overnight. The dried polymer was sampled for analysis by gel permeation chromatography, bottled and stored in a desiccator.

EXAMPLE 8

This Example illustrates the synthesis of a hydrophilic reactive polymer having a brush or branched structure with DMA chains pendent from the backbone of the polymer. The polymer consisted of the combination of the DMA macromonomer, glycidyl methacrylate, and DMA monomer, prepared as follows. To a reaction flask were added distilled N,N-dimethylacrylamide (DMA, 32 g, 0.32 moles), DMA macromer from Example 5 in the amount of 4 g (0.0008 moles), distilled glycidyl methacrylate (GM, 4.1 g, 0.029 moles), Vazo-64 (AIBN, 0.06 g, 0.00037 moles) and toluene (500 ml). The reaction vessel was fitted with a magnetic stirrer, condenser, thermal controller, and a nitrogen inlet. Nitrogen was bubbled through the solution for 15 min to remove any dissolved oxygen. The reaction flask was then heated to 60° C. under a passive blanket of nitrogen for 20 hours. The reaction mixture was then added slowly to 4 liters of ethyl ether with good mechanical stirring. The reactive polymer precipitated and was collected by vacuum filtration. The solid was placed in a vacuum oven at 30° C. overnight to remove the ether, leaving 33.2 g of reactive polymer (83% yield). The reactive polymer was placed in a desiccator for storage until use.

EXAMPLE 9

This example illustrates the synthesis of a vinylpyrrrolidone-co-4-vinylcyclohexyl-1,2-epoxide polymer (NVP-co-VCH) useful to coat a silicone substrate according to the present invention. The polymer was prepared based on the following reaction scheme:

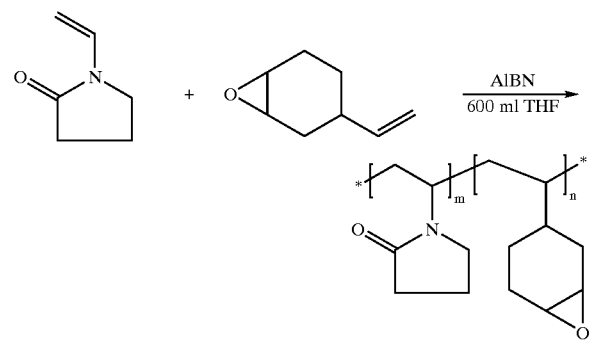

To a 1 liter reaction flask were added distilled N-vinylpyrrolidone (NVP, 53.79 g, 0.48 moles), 4-vinylcyclohexyl-1,2-epoxide (VCHE, 10.43 g, 0.084 moles), Vazo-64 (AIBN, 0.05 g, 0.0003 moles) and THF (600 ml). The reaction vessel was fitted with a magnetic stirrer, condenser, thermal controller, and a nitrogen inlet. Nitrogen was bubbled through the solution for 15 min to remove any dissolved oxygen. The reaction flask was then heated to 60° C. under a passive blanket of nitrogen for 20 hrs. The reaction mixture was then added slowly to 6 liters of ethyl ether with good mechanical stirring. The copolymer precipitated and was collected by vacuum filtration. The solid was placed in a vacuum oven at 30° C. overnight to remove the ether, leaving 21 g of reactive polymer (32% yield). The hydrophilic reactive polymer was placed in a desiccator for storage until use.

EXAMPLE 10

This Example illustrates the synthesis of a hydrophilic reactive (linear) copolymer of DMA/GMA, which is used in Examples 13, 14, and 15 below, according to the following reaction scheme:

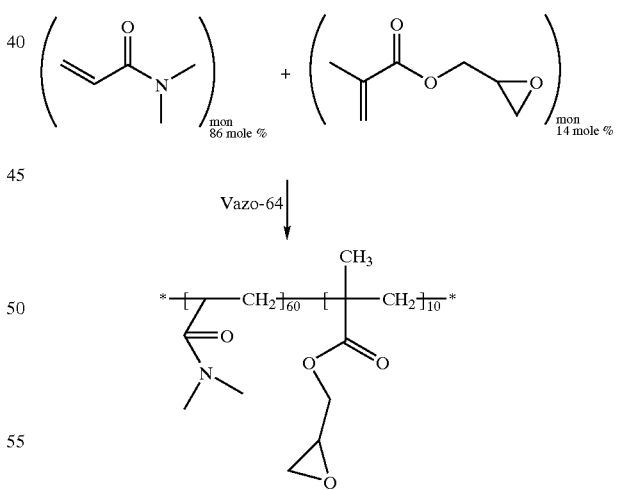

To a 1-liter reaction flask were added distilled N,N-dimethylacrylamide (DMA, 48 g, 0.48 moles), distilled glycidyl methacrylate (GM, 12 g, 0.08 moles), Vazo-64 (AIBN, 0.096 g, 0.0006 moles) and toluene (600 ml). The reaction vessel was fitted with a magnetic stirrer, condenser, thermal controller, and a nitrogen inlet. Nitrogen was bubbled through the solution for 15 min to remove any dissolved oxygen. The reaction flask was then heated to 60° C. under a passive blanket of nitrogen for 20 hours. The reaction mixture was then added slowly to 6 liters of ethyl ether with good mechanical stirring. The reactive polymer precipitated and was collected by vacuum filtration. The solid was placed in a vacuum oven at 30° C. overnight to remove the ether leaving 50.1 g of reactive polymer (83% yield). The reactive polymer was placed in a desiccator for storage until use.

EXAMPLE 11

This Example illustrates the synthesis of a water-soluble reactive polymer of DMA/OFPMA/GMA, according to the following reaction scheme:

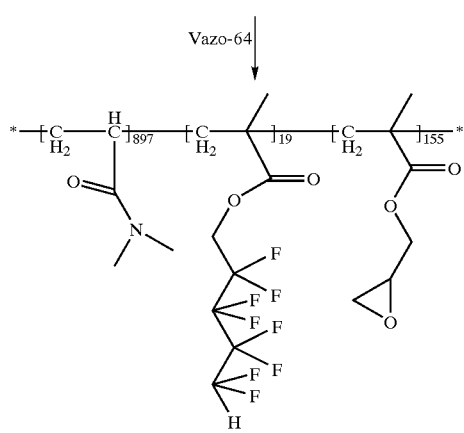

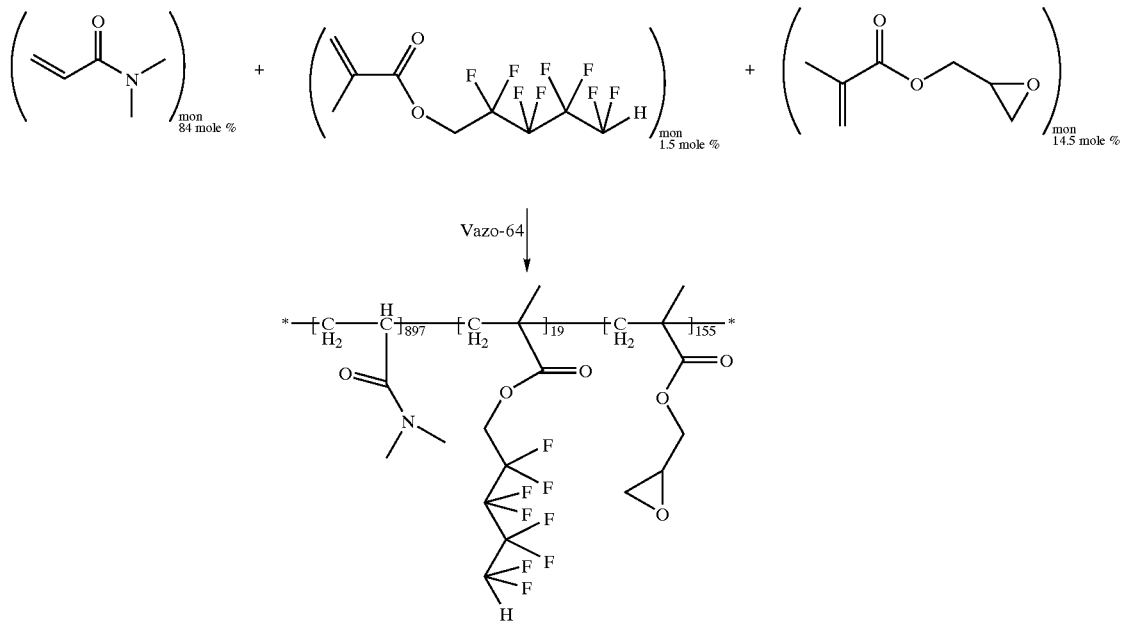

To a 500 ml reaction flask were added distilled N,N-dimethylacrylamide (DMA,16 g, 0.16 moles), 1H,1H,5H-octafluoropentylmethacrylate (OFPMA,1 g, 0.003 moles, used as received), distilled glycidyl methacrylate (GM, 4 g, 0.028 moles) Vazo-64 (AIBN, 0.03 g, 0.00018 moles) and toluene (300 ml). The reaction vessel was fitted with a magnetic stirrer, condenser, thermal controller, and a nitrogen inlet. Nitrogen was bubbled through the solution for 15 minutes to remove any dissolved oxygen. The reaction flask was then heated to 60° C. under a passive blanket of nitrogen for 20 hours. The reaction mixture was then added slowly to 3 liters of ethyl ether with good mechanical stirring. The reactive polymer precipitated and was collected by vacuum filtration. The solid was placed in a vacuum oven at 30° C. overnight to remove the ether leaving 19.3 g of reactive polymer (92% yield). The reactive polymer was placed in a desiccator for storage until use.

EXAMPLE 12

This Example illustrates the synthesis of a hydrophilic reactive polymer of DMA/MAA, according to the following reaction scheme:

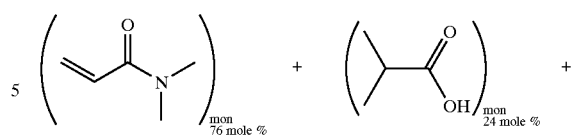

-continued

To a 500 ml reaction flask were added distilled N,N-dimethylacrylamide (DMA, 16 g, 0.16 moles), methacrylic acid (MAA, 4 g, 0.05 moles) Vazo-64 (AIBN, 0.033 g, 0.0002 moles) and anhydrous 2-propanol (300 ml). The reaction vessel was fitted with a magnetic stirrer, condenser, thermal controller, and nitrogen inlet. Nitrogen was bubbled through the solution for 15 minutes to remove any dissolved oxygen. The reaction flask was then heated to 60° C. under a passive blanket of nitrogen for 72 hours. The reaction mixture was then added slowly to 3 liters of ethyl ether with good mechanical stirring. The reactive polymer precipitated and was collected by vacuum filtration. The solid was placed in a vacuum oven at 30° C. overnight to remove the ether leaving 9.5 g of reactive polymer (48% yield). The reactive polymer was placed in a desiccator for storage until use.

EXAMPLE 13

This Example illustrates the surface treatment of Balafilcon A contact lenses (PureVision® lenses, commercially available from Bausch & Lomb, Inc., Rochester, N.Y.) made from the material of Example 1, which surface treatment employed the hydrophilic reactive polymers made from Example 10 above, according to the following reaction scheme:

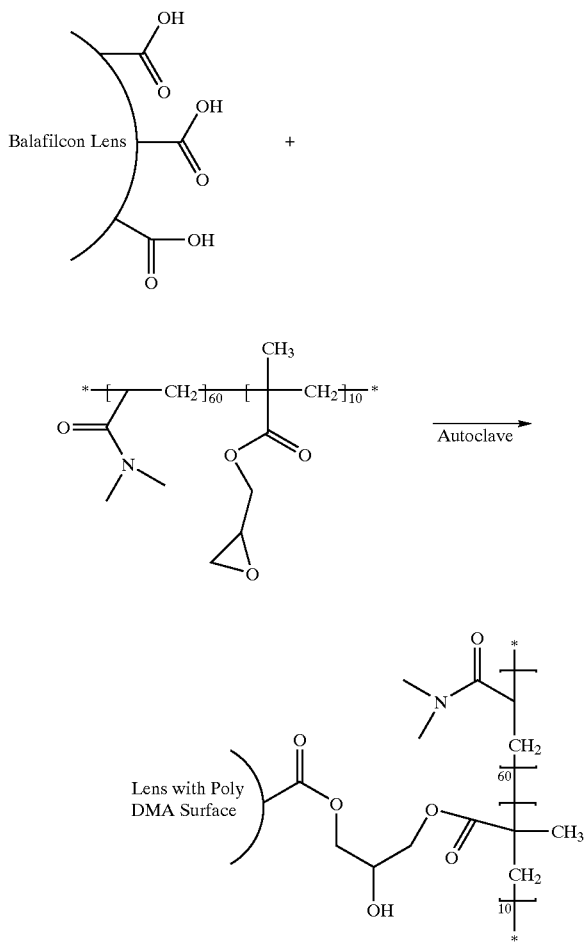

A solution of reactive polymer of Example 10 (10.0 g per 1000 ml of water) was prepared. Lenses were extracted with three changes of 2-propanol over a four-hour period and then with three changes of water at one-hour intervals. Lenses (36 samples) were then placed in the solution of reactive polymer. One drop of methyldiethanolamine was added to catalyze the reaction. The lenses were put through one 30-minute autoclave cycle.

EXAMPLE 14

This Example illustrates the surface treatment of an RGP Lens Surface according to the present invention, as shown below. The material was Boston® XO (hexafocon A) lens, commercially available from Bausch & Lomb, Inc.

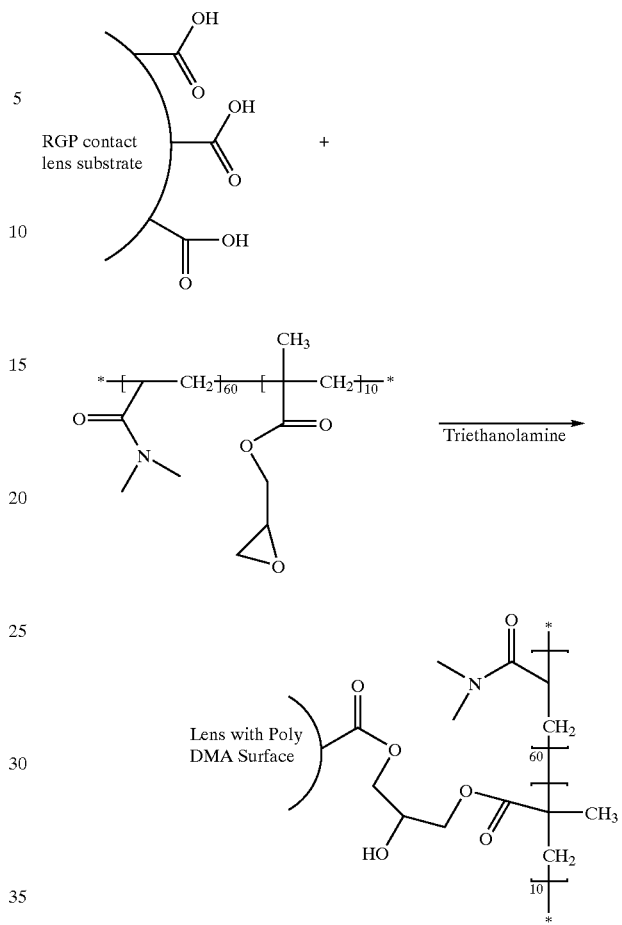

A solution of reactive polymer of Example 10 (5.0 g per 100 ml of water) was prepared. Lenses (20 samples) were then placed in the solution of reactive polymer with two (2) drops of triethanolamine and heated to 55° C. for one (1) hour. The surface-coated lenses were then rinsed off twice with purified water and allowed to dry. A drop of water placed on an untreated lens would bead up and roll off the surface while a drop of water was placed on the treated lens spread completely, wetting the lens surface.

X-ray Photo Electron Spectroscopy (XPS) data was obtained at the Surface Science lab within Bausch and Lomb. A Physical Electronics [PHI] Model 5600 XPS was used for the surface characterization. This instrument utilized a monochromated A1 anode operated a 300 watts, 15 kV and 20 milliamps. The base pressure of the instrument was $2.0 \times 10^{-10}$ torr and during operation the pressure was $5.0 \times 10^{-8}$ torr. This instrument made use of a hemispherical analyzer. The instrument had an Apollo workstation with PHI 8503A version 4.0A software. The practical measure for sampling depth for this instrument at a sampling angle of 45° was 74 Å.

Each specimen was analyzed utilizing a low-resolution survey spectra (0–1100 eV) to identify the elements present on the sample surface (10–100Å). Surface elemental compositions were determined from high-resolution spectra obtained on the elements detected in the low-resolution survey scans. Those elements included oxygen, nitrogen, carbon, silicon and fluorine. Quantification of elemental compositions was completed by integration of the photoelectron peak areas after sensitizing those areas with the instrumental transmission function and atomic cross sections for the orbitals of interest. The XPS data for the coated lenses and controls are given in Table 3 below.

TABLE 3

| Sample | | O | N | C | Si | F |
|---|---|---|---|---|---|---|
| Lens Posterior | Average | 22.3 | 4.8 | 54.4 | 10.3 | 10.9 |
| | Std dev | | | | | |
| Lens Anterior | Average | 19.1 | 6.7 | 63.4 | 2.7 | 8.1 |
| | std dev | 0.6 | 0.3 | 1.1 | 0.6 | 0.7 |
| Boston ® XO | Average | 18.7 | 0.0 | 56.1 | 5.2 | 20.0 |
| (post & ant are the same) | std dev | 0.5 | 0.0 | 0.7 | 0.3 | 0.4 |
| Theoretical Atomic Concentrations for DMA-co-GMA Reactive Polymer | | 17 | 12 | 71 | 0 | 0 |

EXAMPLE 15

Figure 2:
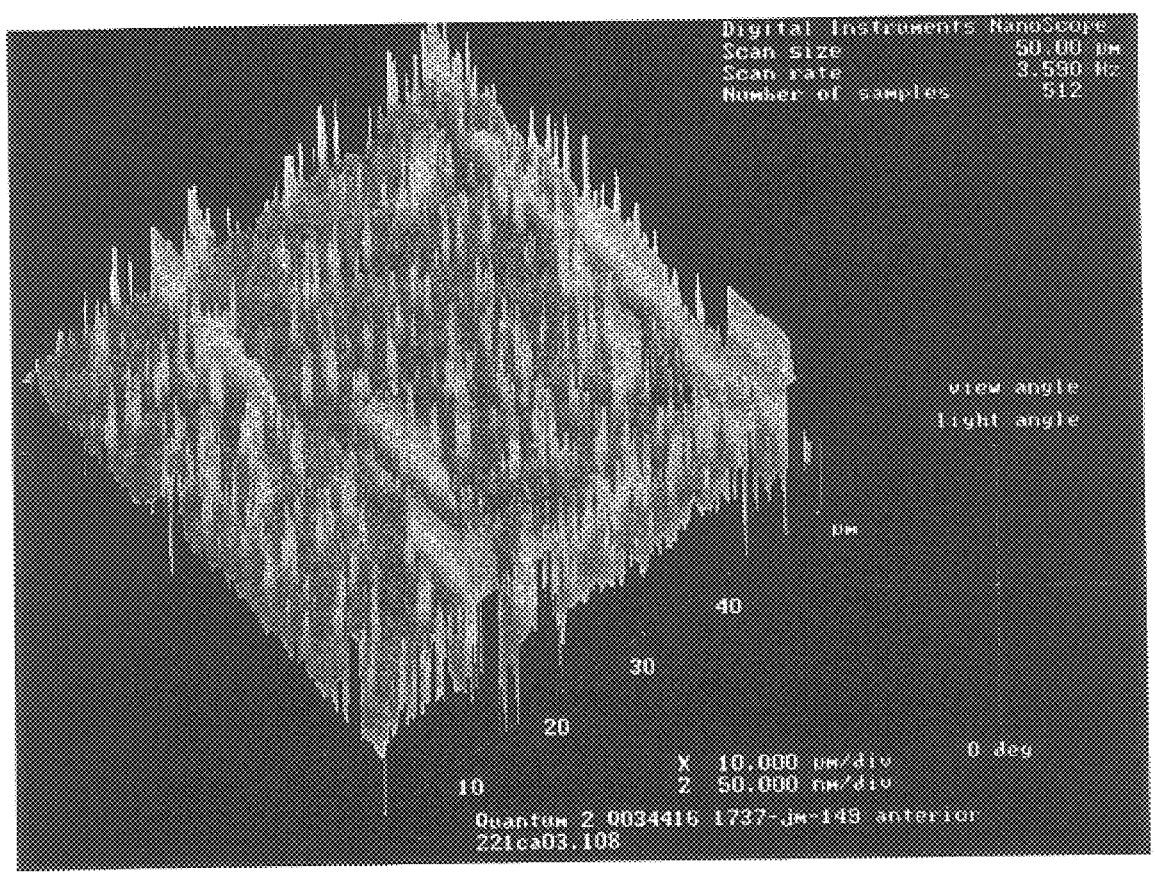
FIG. 2 shows an Atomic Force Microscopy (AFM) topographical image (50 $\mu m^2$) of a contact lens coated described in Example 14 according to one embodiment of the present invention, which lens is a silicone rigid-gas-permeable lens coated with a polymer as described in Example 10, a copolymer of dimethyl acrylamide and glycidyl methacrylate.
Figure 3:
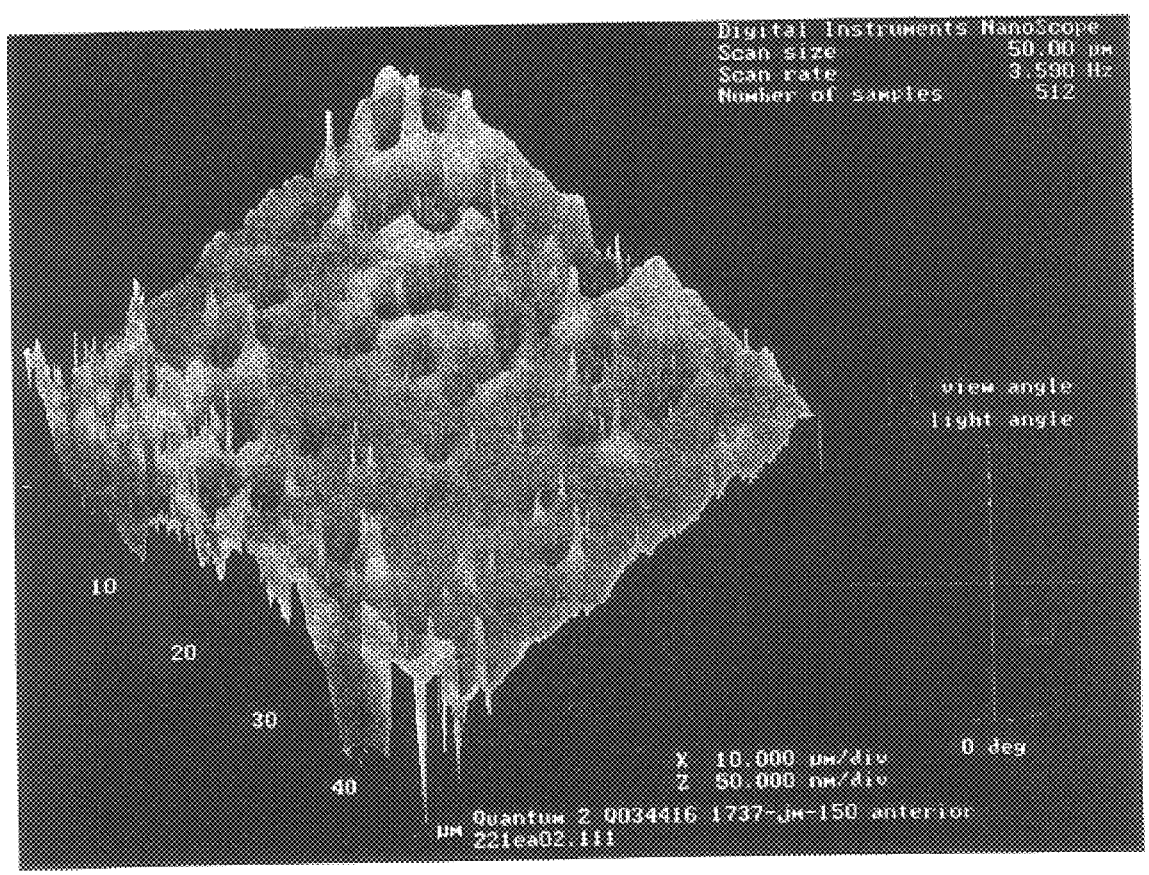
FIG. 3 shows an Atomic Force Microscopy (AFM) topographical image (50 $\mu m^2$) of a contact lens coated described in Example 15 according to one embodiment of the present invention, which lens is a silicone rigid-gas-permeable lens coated with a combination of the hydrophilic copolymers described in Examples 10 and Example 12.

This Example illustrates another surface treatment of an Boston® XO contact lens material, commercially available from Bausch & Lomb, Inc., according to the following reaction sequence:

A solution of reactive polymers of Example 10 and Example 12 above (2.5 g of each polymer per 100 ml of water) was prepared. The mixture of polymers was used in an attempt to build a thicker polymer coating via a layering effect. Lenses (20 samples) were then placed in the solution of reactive polymer with two drops of triethanolamine and heated to 55° C. for one hour. The surface-coated lenses were then rinsed off twice with purified water and allowed to dry. A drop of water placed on an untreated lens would bead up and roll off the surface while a drop of water placed on the treated lens spread completely wetting the lens surface. Atomic Force Microscopy (AFM) analysis suggests that the combination of polymers gave a thicker polymer coating. Comparisons between a Boston® XO lens with no polymer coating (FIG. 1), the polymer coating of Example 14 (FIG. 2), and the coating of this Example 15 (FIG. 3) are shown in FIGS. 1 to 3.

X-ray Photo Electron Spectroscopy (XPS) data was obtained at the Surface Science lab within Bausch and Lomb. A Physical Electronics [PHI] Model 5600 XPS was used for the surface characterization. This instrument utilized a monochromated A1 anode operated a 300 watts, 15 kV and 20 milliamps. The base pressure of the instrument was $2.0 \times 10^{-10}$ torr and during operation the pressure was

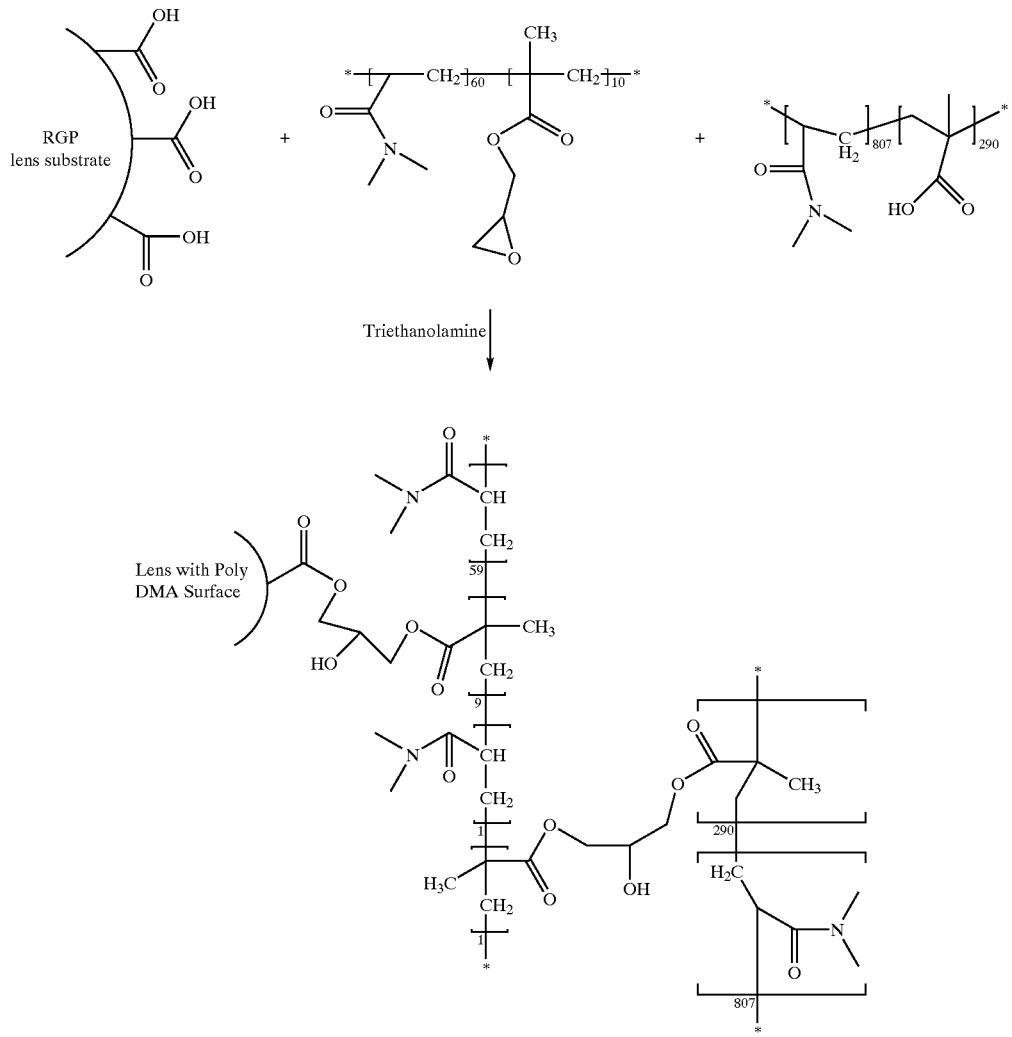

5.0×10$^{-8}$ torr. This instrument made use of a hemispherical analyzer. The instrument had an Apollo workstation with PHI 8503A version 4.0A software. The practical measure for sampling depth for this instrument at a sampling angle of 45° was 74 Å.

Each specimen was analyzed utilizing a low-resolution survey spectra (0–1100 eV) to identify the elements present on the sample surface (10–100Å). Surface elemental compositions were determined from high-resolution spectra obtained on the elements detected in the low-resolution survey scans. Those elements included oxygen, nitrogen, carbon, silicon and fluorine. Quantification of elemental compositions was completed by integration of the photoelectron peak areas after sensitizing those areas with the instrumental transmission function and atomic cross sections for the orbitals of interest. The XPS data for the coated lenses and controls are given in Table 4A below.

EXAMPLE 16

This Example illustrates the surface treatment of Balafilcon A contact lenses (PureVision® lenses, commercially available from Bausch & Lomb, Inc., Rochester, N.Y.) made from the material of Example 1, which surface treatment employed the hydrophilic reactive polymers made from Example 11 above, according to the following reaction scheme:

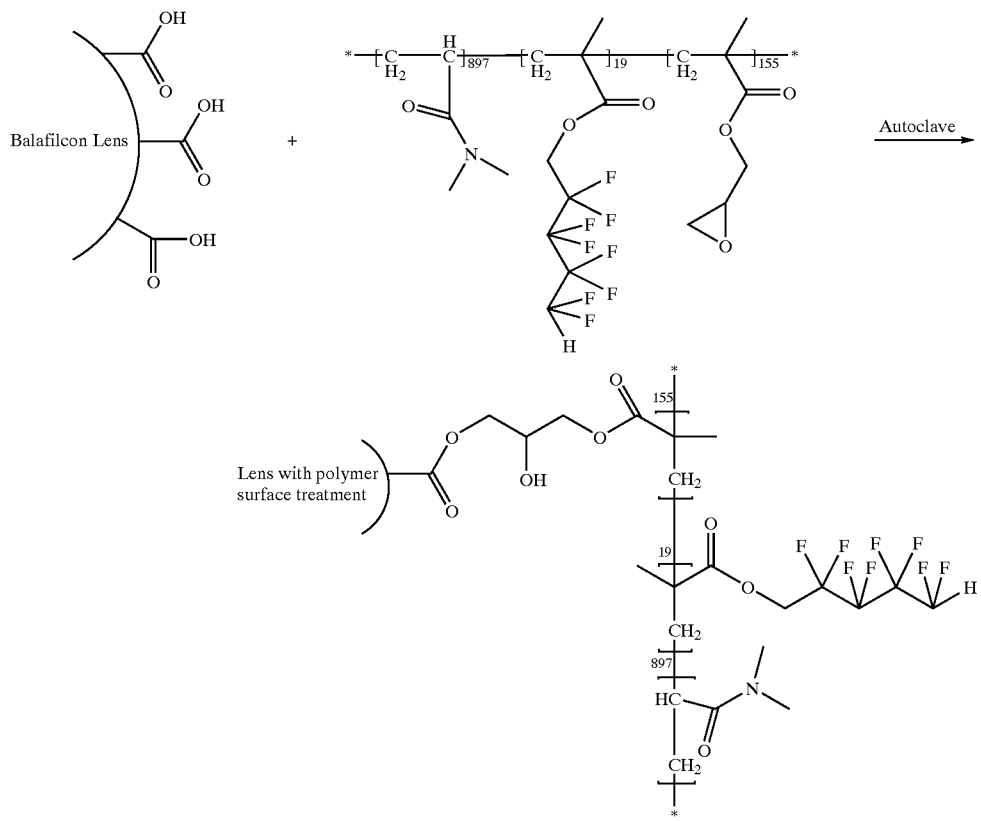

Two solutions of the reactive polymer of Example 11 were prepared (see Table 4B below). Lenses were extracted in 2-propanol for 4 hours and then placed in purified water for 10 minutes. The water bath was then changed, and the lenses were allowed to soak for an additional 10 minutes. Lenses (30 samples) were then placed in each solution of reactive polymer with one drop of methyldiethanolamine to catalyze the reaction. The lenses were put through one 30-minute autoclave cycle. The solution in the vials was then replaced with purified water twice, and the samples were again autoclaved. This procedure was used to remove any hydrophilic polymer not chemically bonded to the lens.

TABLE 4A

| Sample | | O | N | C | Si | F |
|---|---|---|---|---|---|---|
| Lens Posterior | Average | 18.8 | 8.0 | 67.6 | 3.7 | 2.6 |
| | std dev | | | | | |
| Lens Anterior | Average | 18.4 | 4.2 | 62.8 | 4.1 | 10.5 |
| | std dev | 0.5 | 1.2 | 1.7 | 0.4 | 3.1 |
| Quantumr ® II Control (post & ant are the same) | Average | 18.7 | 0.0 | 56.1 | 5.2 | 20.0 |
| | std dev | 0.5 | 0.0 | 0.7 | 0.3 | 0.4 |
| Theoretical Atomic Concentrations for DMA-co-GMA Reactive Polymer | | 17 | 12 | 71 | 0 | 0 |

TABLE 4B

| Sample | Polymer Concentration | No. Lenses treated |
|---|---|---|
| A | 1.0% (2.5 g/250 ml H$_2$O) | 30 |
| B | 2.0% (5 g/250 ml H$_2$O) | 30 |
| Control | None | 30 |

Figure 4:
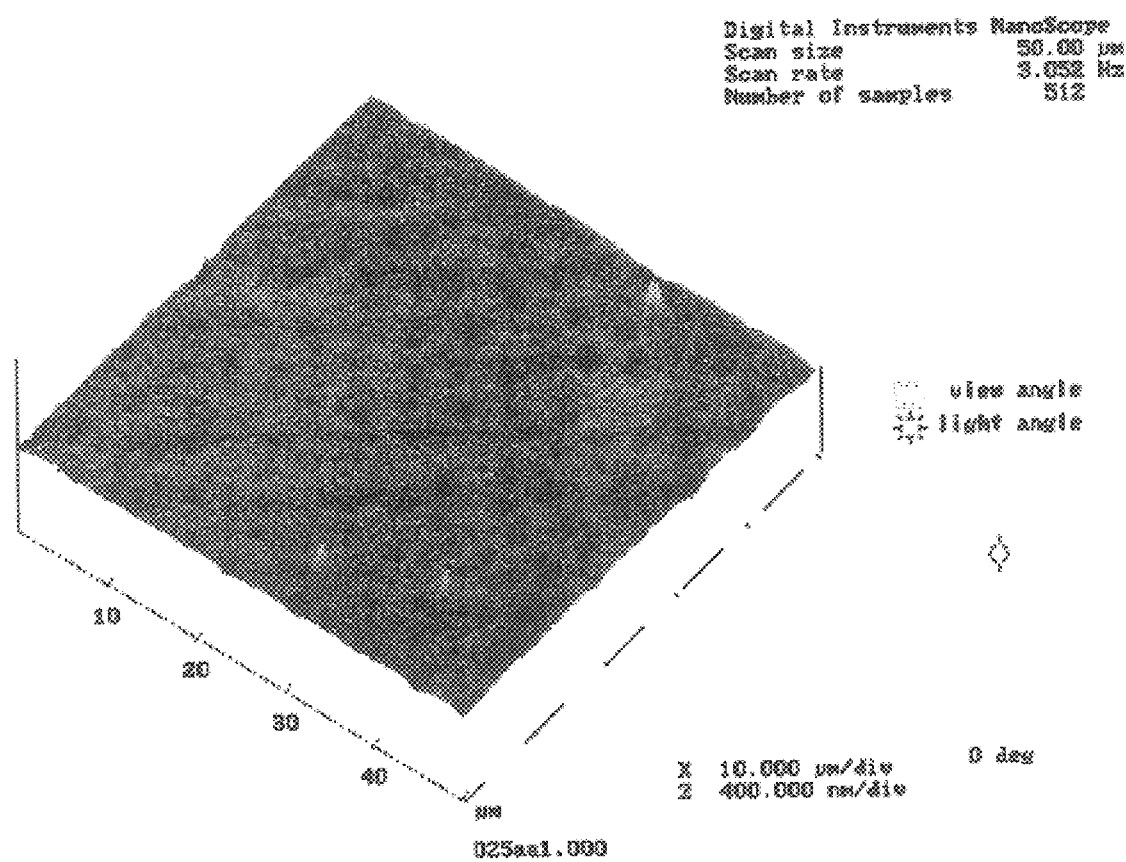
FIG. 4 shows Atomic Force Microscopy (AFM) topographical image (50 $\mu m^2$) of a control contact lens described in Example 16 for comparison to other lenses according to another embodiment of the present invention, which lens is a silicone hydrogel lens coated with a polymer as described in Example 11.
Figure 5:
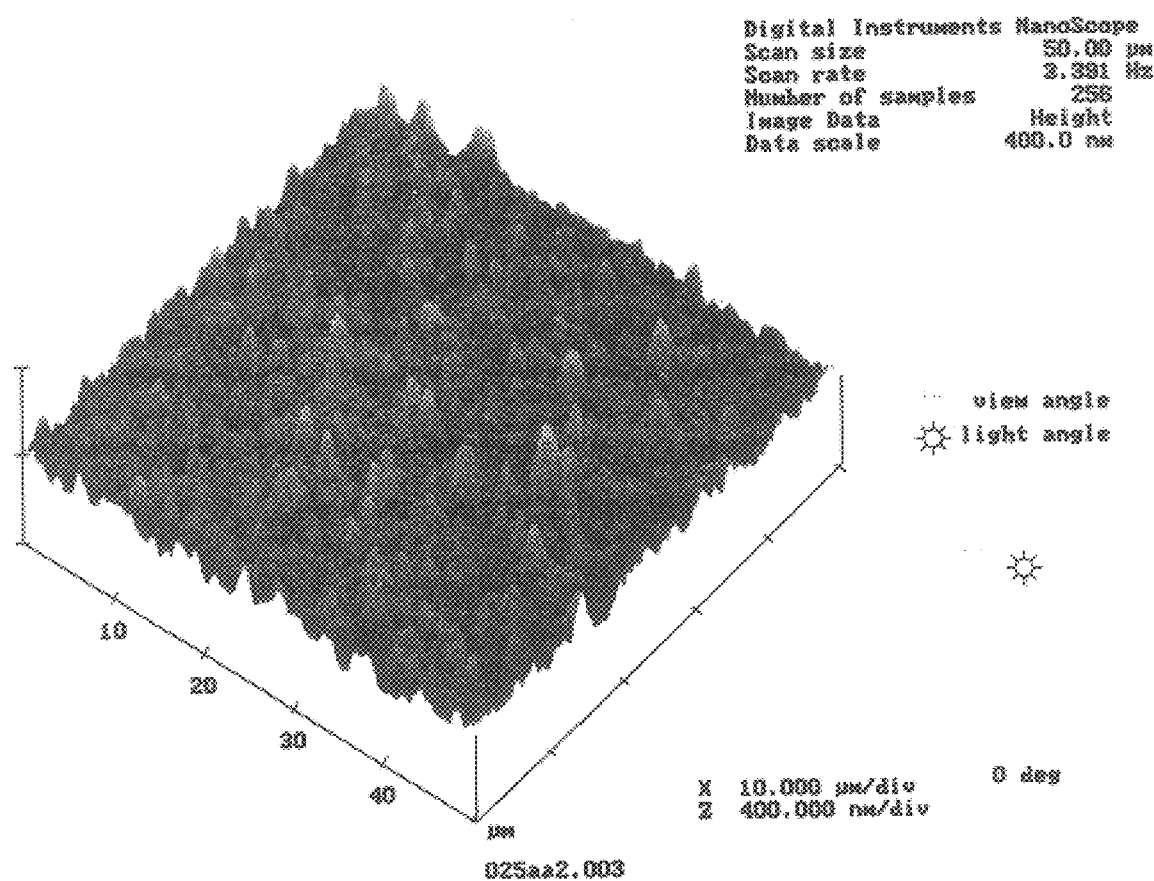
FIG. 5 shows Atomic Force Microscopy (AFM) topographical image (50 $\mu m^2$) of a contact lens coated described in Example 16 according to one embodiment of the present invention, which lens is a silicone hydrogel lens coated with a polymer as described in Example 11, a copolymer of dimethyl acrylamide, glycidyl methacrylate, and octafluoropentylmethacrylate.
Figure 6:
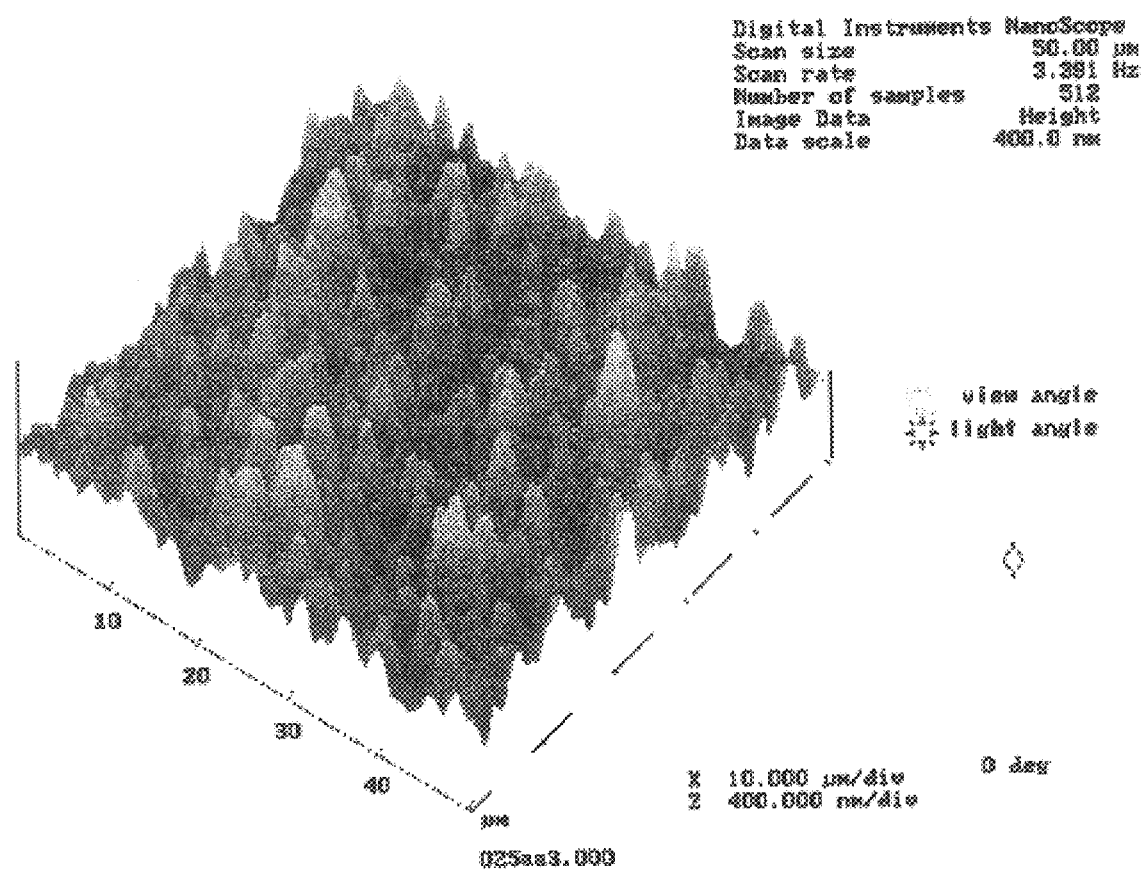
FIG. 6 shows Atomic Force Microscopy (AFM) topographical image (50 $\mu m^2$) of a contact lens coated described in Example 16 according to one embodiment of the present invention, which lens is a silicone hydrogel lens coated with a polymer as described in Example 11, a copolymer of dimethyl acrylamide, glycidyl methacrylate, and octafluoropentylmethacrylate, which is used for coating at a higher concentration than was used for coating the lens in FIG. 5.

The atomic force microscopy (AFM) images of the control is shown in FIG. 4. FIG. 5 and FIG. 6 show the surface of Samples A and B, respectively. The hydrophilic coating is clearly shown in FIGS. 5 and 6 compared to the surface image of the Control Sample. Elemental analysis by XPS also indicates that the material surface has been modified. The XPS data was obtained at the Surface Science lab within Bausch and Lomb. A Physical Electronics [PHI] Model 5600 XPS was used for the surface characterization. This instrument utilized a monochromated Al anode operated a 300 watts, 15 kV and 20 milliamps. The base pressure of the instrument was $2.0 \times 10^{-10}$ torr and during operation the pressure was $5.0 \times 10^{-8}$ torr. This instrument made use of a hemispherical analyzer. The instrument had an Apollo workstation with PHI 8503A version 4.0A software. The practical measure for sampling depth for this instrument at a sampling angle of 45° was 74 Å.

Each specimen was analyzed utilizing a low-resolution survey spectra (0–1100 eV) to identify the elements present on the sample surface (10–100Å). Surface elemental compositions were determined from high-resolution spectra obtained on the elements detected in the low-resolution survey scans. Those elements included oxygen, nitrogen, carbon, silicon and fluorine. Quantification of elemental compositions was completed by integration of the photoelectron peak areas after sensitizing those areas with the instrumental transmission function and atomic cross sections for the orbitals of interest. The XPS data is given in Table 4C below.

TABLE 4C

| Sample | | O1s | N1s | C1s | Si2p | F1s |
|---|---|---|---|---|---|---|
| Control Posterior | Average | 17.7 | 7.2 | 66.9 | 8.1 | 0.0 |
| | std dev | 0.9 | 0.2 | 0.8 | 0.3 | 0.0 |
| Control Anterior | Average | 17.9 | 7.0 | 66.9 | 8.2 | 0.0 |
| | std dev | 0.6 | 0.6 | 0.7 | 0.4 | 0.0 |
| A Posterior | Average | 17.9 | 8.9 | 69.5 | 1.8 | 2.0 |
| | std dev | 0.3 | 0.2 | 0.6 | 0.6 | 0.2 |
| A Anterior | Average | 17.7 | 9.1 | 69.7 | 1.7 | 1.9 |
| | std dev | 0.3 | 0.3 | 0.8 | 0.3 | 0.2 |
| B Posterior | Average | 18.0 | 8.9 | 69.9 | 1.2 | 2.1 |
| | std dev | 0.3 | 0.5 | 1.0 | 0.1 | 0.4 |
| B Anterior | Average | 17.8 | 8.8 | 70.0 | 1.3 | 2.0 |
| | std dev | 0.2 | 0.3 | 0.6 | 0.3 | 0.0 |
| Theoretical Atomic Conc. DMA-co-OFPMA-co-GMA From Example 11 | | 17.1 | 11.0 | 70.1 | 0.0 | 1.8 |

EXAMPLE 17

This Example illustrates improved inhibition of lipid deposition for the Balafilcon A lenses (PureVision® lenses) coated by reaction with various hydrophilic reactive polymers according to the present invention. Sample E lenses was coated using a 1% solution of the DMA/OFPMA/GM copolymer of Example 11, and Sample EE lenses was coating using a 2% solution of the same polymer. Samples F and FF lenses were respectfully coated using 1% and 2% solutions of the DMA/GM copolymer of Example 10. The lenses were placed in an aqueous solution of the reactive hydrophilic polymer with a catalyst and run through one autoclave cycle. The lenses were then rinsed in HPLC grade water, placed in fresh HPLC water, and autoclaved for a second time. The control lenses (no surface treatment) were placed in HPLC water and autoclaved. One control lens was the Balafilcon A lens prior to any surface treatment. A second control lens was the commercial PureVisiono lens with a oxidative plasma surface treatment. For the lipid analysis, Gas Chromatography (GC) was employed, including an HP Ultra 1 column with an FID detector and He carrier gas. In the in vitro lipid deposition protocol, six lenses were subject to deposition for each of the lens types tested, employing a lipid mix of palmitic acid methyl ester, cholesterol, squalene and mucin in MOPS buffer. Mucin was utilized as a surfactant to aid in the solubilization of the lipids. The above lipid mix in the amount of 1.5 ml was added to the test lenses, which were subject to deposition in a 37° C. shaking-water bath for 24 hours. The lenses were then removed from the water bath, rinsed with ReNu® Saline to remove any residual deposition solution, and placed in glass vials for extraction. A three hour 1:1 $CHCl_3$/MeOH extraction was subsequently followed by a three hour hexane extraction. Extracts were then combined and run on the GC chromatograph. Standard solutions of each of the lipids in the deposition mix were made in 1:1 $CHCl_3$/MeOH and run on the GC for determination of the concentration of lipid extracted from the lenses. The in vitro lipid deposition profiles for the lenses tested, using the protocol above, are shown in Table 5 below.

TABLE 5

| Sample | Average Lipid Concentration* ($\mu$g) |
|---|---|
| E | 39.9 |
| EE | 36.7 |
| F | 51.2 |
| FF | 39.6 |
| Plasma-Oxidation Control | 117 |
| No-Surface-Treatment Control lenses | 243.3 |

*The average represents the deposition profile for 6 deposited lenses.

The results indicate that lenses coated according to the present invention can exhibit reduced lipid deposition, a particularly advantageous property for continuous-wear hydrogel lenses.

EXAMPLE 18

Procedure

A solution was prepared, of reactive polymer, N,N-dimethylacrylamide-co-glycidyl methacrylate (0.4 g/20 ml of HPLC water) and eight drops of triethanolamine. Polished buttons (4 samples) were imaged by non-contact atomic force microscopy then cleaned by rubbing with HPLC grade water. The substrates were then placed in the 4–5 ml of reactive polymer solution, in sealed lens flat packs and heated to 55° C. for one hour. The treated polymer buttons were then rinsed off twice with HPLC water and allowed to dry. A drop of water placed on an untreated lens would bead up and roll off the surface while a drop of water was placed on the treated lens spread completely wetting the lens surface.

The buttons were then cleaned with 3–4 drops of Bostono Advance brand contact lens cleaner, a sterile surfactant solution containing silica gel as an abrasive-cleaning agent, followed by rinsing (2 times with) HPLC grade water. The polymer buttons were allowed to dry and AFM images were again recorded. The images appeared to be equivalent to those taken before any coating was applied.

The coating procedure outlined above was repeated and AFM images were recorded. The material again appeared to be coated with polymer.

The procedure of this Example 18 was repeated with three fresh RGP contact lens material buttons. Surface analysis for the repeated experiment was x-ray photoelectron spectroscopy (XPS). The XPS data is given in the table below. It is clearly evident from the data given below, looking at the increase of nitrogen (N, from the coating polymer) and the corresponding decreases of silicon (Si) and fluorine (F) in the substrate, that the polymer coating was applied, removed and applied again.

TABLE 6

XPS Results for Example 18

| Sample | O | N | C | Si | F | |
|---|---|---|---|---|---|---|
| Button Before Coating | 17.9 | 0.0 | 57.9 | 5.7 | 18.5 | button 1 |
| | 18.2 | 0.0 | 54.8 | 5.3 | 20.7 | |
| | 18.9 | 0.0 | 52.7 | 5.3 | 23.0 | button 2 |
| | 17.5 | 0.0 | 55.1 | 6.0 | 21.5 | button 3 |
| | 18.9 | 0.0 | 54.0 | 6.2 | 20.9 | button 4 |
| | 18.1 | 0.0 | 54.3 | 5.9 | 21.7 | |
| Average | 18.3 | 0.0 | 54.8 | 5.7 | 21.0 | |
| Standard Deviation | 0.6 | 0.0 | 1.7 | 0.4 | 1.5 | |
| Coated Button | 19.8 | 4.9 | 66.7 | 2.8 | 5.8 | button 1 |
| | 19.7 | 6.0 | 66.3 | 2.5 | 5.6 | |
| | 20.3 | 6.3 | 66.1 | 2.6 | 4.8 | button 2 |
| | 20.5 | 5.2 | 65.1 | 2.8 | 6.4 | button 3 |
| | 18.6 | 3.3 | 76.1 | 1.3 | 0.8 | button 4 |
| | 16.8 | 4.3 | 78.9 | 0.0 | 0.0 | |
| Average | 19.3 | 5.0 | 69.8 | 2.0 | 3.9 | |
| Standard Deviation | 1.4 | 1.1 | 6.0 | 1.1 | 2.8 | |
| Button After Removal | 20.4 | 0.0 | 59.3 | 4.7 | 15.6 | button 1 |
| of Coating | 21.3 | 0.0 | 60.4 | 5.0 | 13.4 | |
| | 18.3 | 0.0 | 58.6 | 5.7 | 17.5 | button 2 |
| | 18.5 | 0.0 | 56.2 | 6.1 | 19.2 | button 3 |
| | 19.5 | 0.0 | 56.6 | 6.5 | 17.4 | button 4 |
| | 18.6 | 0.0 | 57.9 | 5.8 | 17.7 | |
| Average | 19.4 | 0.0 | 58.2 | 5.6 | 16.8 | |
| Standard Deviation | 1.2 | 0.0 | 1.6 | 0.7 | 2.0 | |
| Button After Re-coating | 20.6 | 3.2 | 74.1 | 1.4 | 0.7 | button 1 |
| | 20.6 | 3.7 | 74.2 | 0.9 | 0.5 | |
| | 24.6 | 5.1 | 67.1 | 1.9 | 1.4 | button 2 |
| | 19.9 | 5.6 | 69.0 | 2.5 | 3.0 | button 3 |
| | 21.1 | 3.3 | 73.3 | 1.2 | 1.1 | button 4 |
| | 20.5 | 4.9 | 65.5 | 3.6 | 5.5 | |
| Average | 21.2 | 4.3 | 70.5 | 1.9 | 2.0 | |
| Standard Deviation | 1.7 | 1.0 | 3.8 | 1.0 | 1.9 | |

Figure 7:
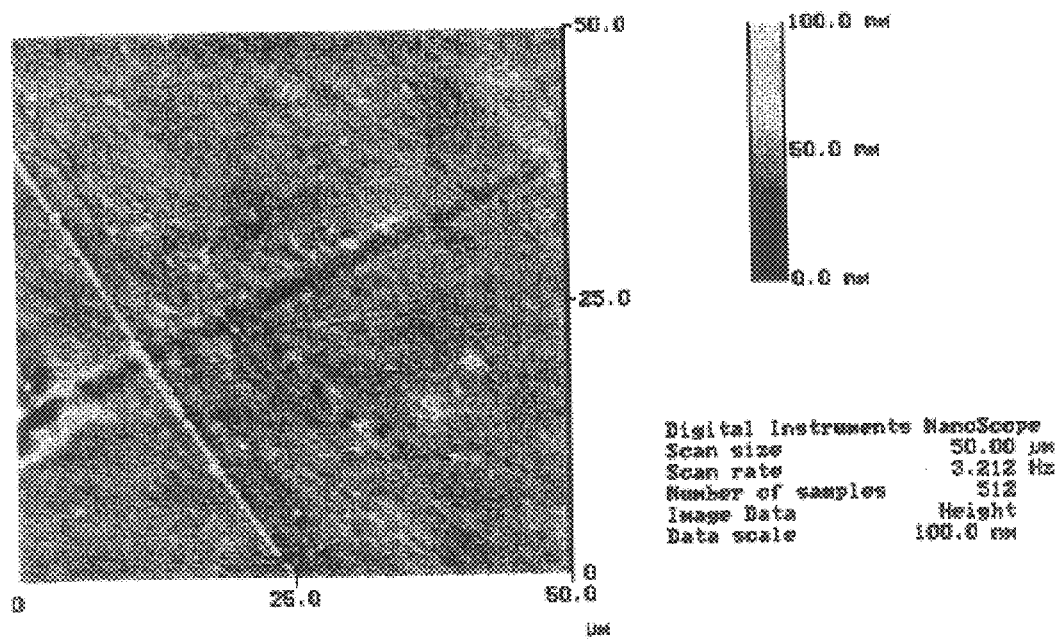
FIG. 7 is an Atomic Force Microscopy (AFM) topographical image (50 $\mu m^2$) of an RGP contact lens material button of Example 18 prior to surface treatment.

FIG. 7 is an AFM topographical image (50 $\mu m^2$) of an RGP contact lens material button of Example 18 prior to surface treatment.

Figure 8:
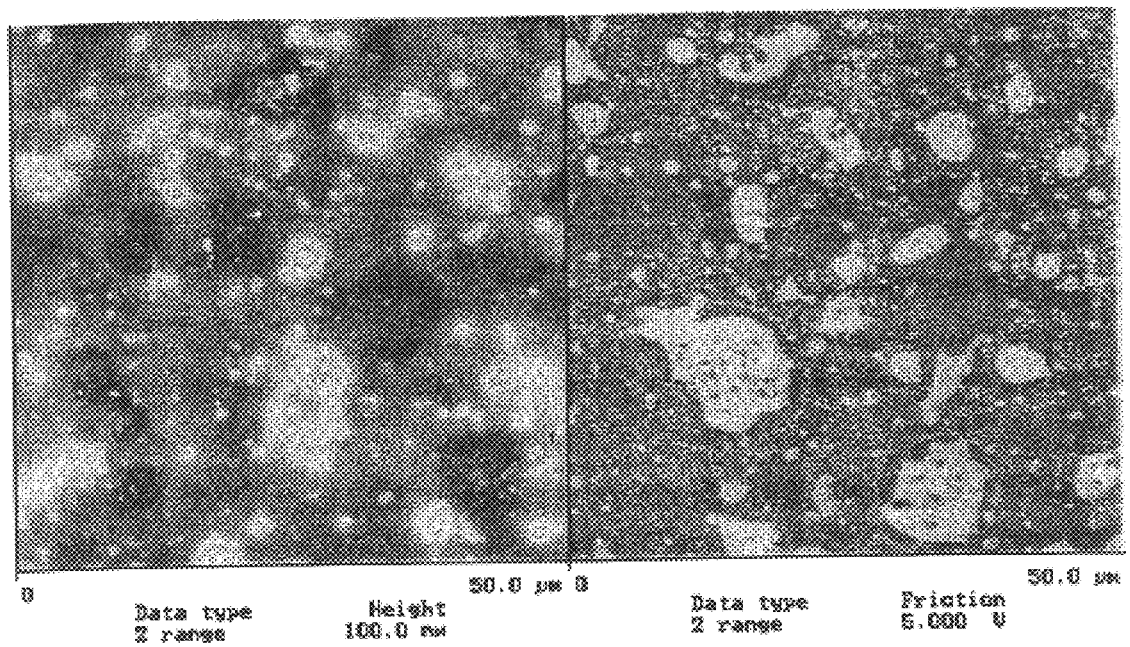
FIG. 8 is an Atomic Force Microscopy (AFM) topographical image (50 $\mu m^2$) of the surface of an RGP button after a first hydrophilic polymer coating step in Example 18.

FIG. 8 is an AFM topographical image (50 $\mu m^2$) of the surface of an RGP button after a first hydrophilic polymer coating step in Example 18.

Figure 9:
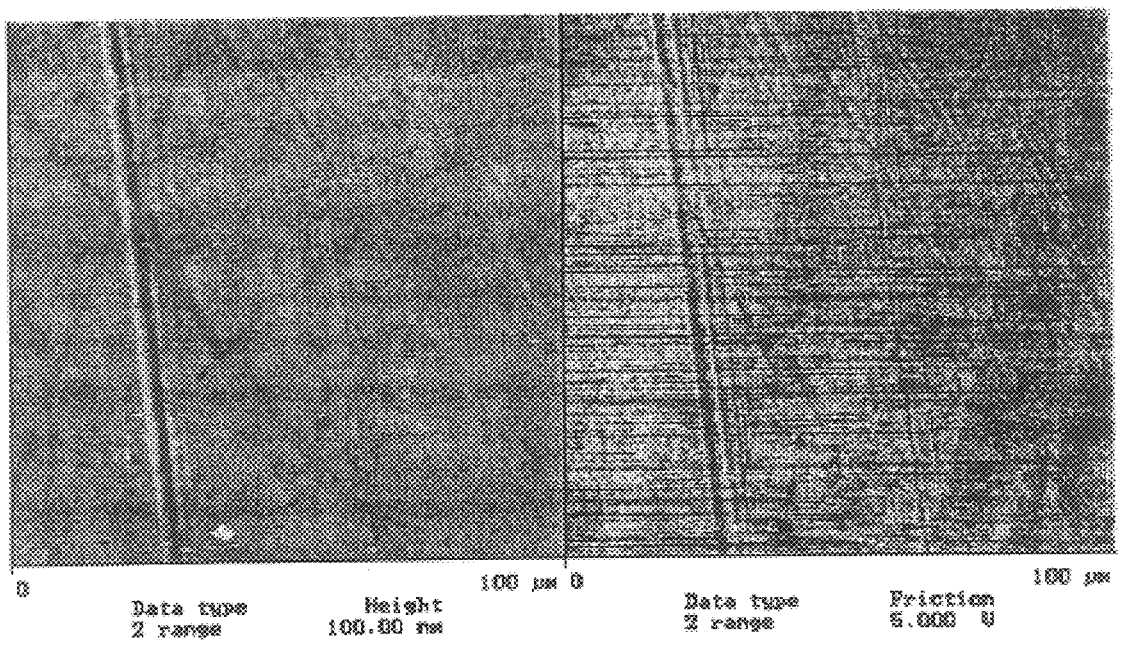
FIG. 9 is an Atomic Force Microscopy (AFM) topographical image (50 $\mu m^2$) of the surface of an RGP button after abrasive removal of the polymer coating in Example 18.

FIG. 9 is an AFM topographical image (50 $\mu m^2$) of the surface of an RGP button after abrasive removal of the polymer coating in Example 18.

Figure 10:
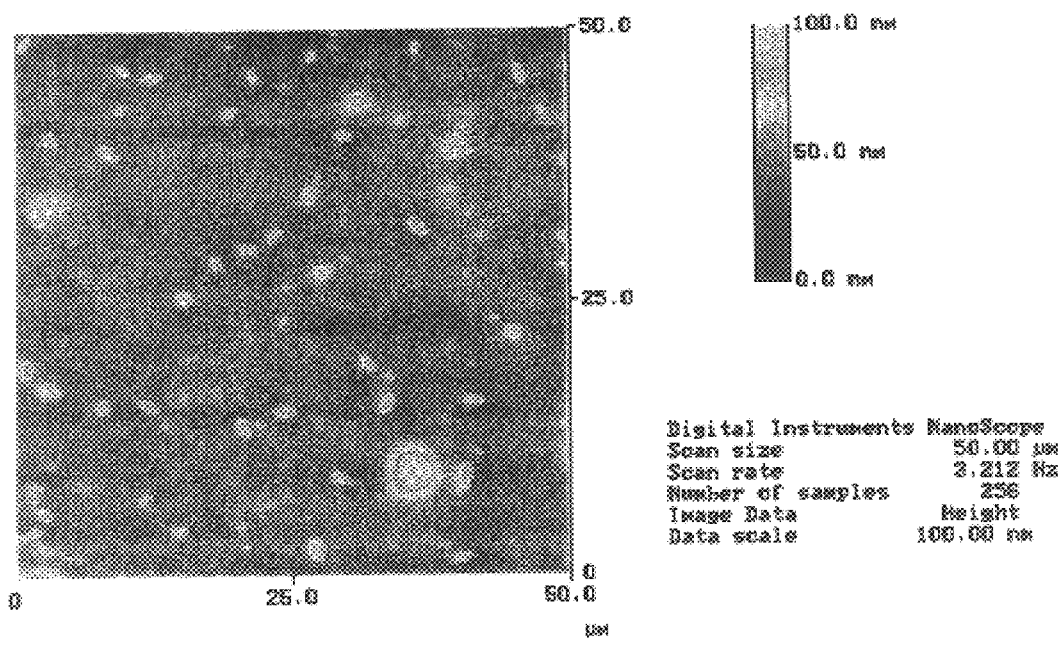
FIG. 10 is an Atomic Force Microscopy (AFM) topographical image (50 $\mu m^2$) of the surface of an RGP button after the hydrophilic polymeric surface was reapplied in Example 18.

FIG. 10 is an AFM topographical image (50 $\mu m^2$) of the surface of an RGP button after the hydrophilic polymeric surface was re-applied in Example 18.

EXAMPLE 19

This Example illustrates the synthesis of the monomer 12-methacryloyloxydodecanoic acid useful in the synthesis of reactive polymers. A reference can be found in the U.S. Pat. No. 4,485,045 by Regen entitled "Sythetic Phosphatidyl Cholines Useful in Forming Liposomes".

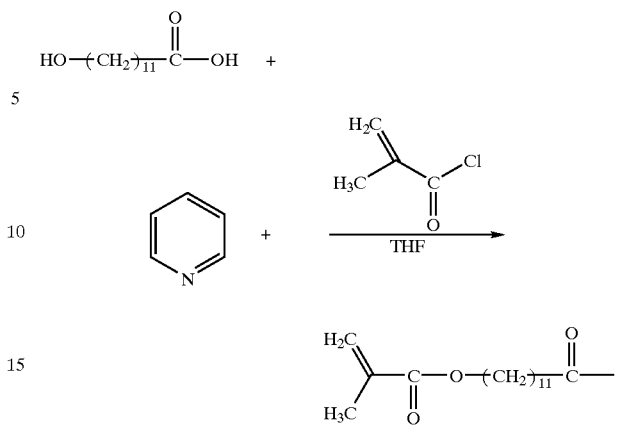

To a 2 liter reaction flask were added 12-hydroxydodecanoic acid (99.5 g, 0.46 moles), anhydrous pryidine (56 ml) and anhydrous tetrahydrofuran (1,000 ml). The mixture was cooled in an ice bath to 0° C. A solution of distilled methacryloyl chloride (48 g, 0.046 moles) in anhydrous tetrahydrofuran (200 ml) was slowly added to the cold reaction mixture with good stirring. Following the addition the mixture was allowed to reach room temperature and left stirring overnight. The solvent was removed by flash evaporation and the residue was taken up in 1 liter of ethyl ether. The ether solution was washed with purified water, dried over magnesium sulfate and again flash evaporated leaving 98.5 grams of crude product. The crude product was further purified by silica gel chromatography using a 1:2 mixture of ethylacetate and heptane to give a 63% yield.

EXAMPLE 20

Example 20 illustrates the synthesis of a hydrophilic reactive polymer of N,N-dimethylacrylamide-co-12-methacryloyloxydodecanoic acid.

To a 500 ml reaction flask were added distilled N,N-dimethylacrylamide (DMA, 15.2 g, 0.153 moles), 12-methacryloxydodecanoic acid (LMAA, 4.8 g, 0.017 moles) Vazo 64 (AIBN, 0.032 g, 0.0002 moles) and anhydrous tetrahydrofuran (200 ml). The reaction vessel was fitted with a magnetic stirrer, condenser, thermal controller and a nitrogen inlet. Nitrogen was bubbled through the solution for 15 minutes to remove any dissolved oxygen. The reaction flask was then heated to 60° C. under a passive blanket of nitrogen for 72 hours. The reaction mixture was then added slowly to 2.5 L of heptane with good mechanical stirring. The reactive polymer precipitated and was collected by vacuum filtration. The solid was placed in a vacuum oven at 30° C. overnight to remove the ether leaving 15 g of reactive polymer (75% yield). The reactive polymer was placed in a desiccator for storage until use.

EXAMPLE 21

This Example illustrates the synthesis of a hydrophilic reactive polymer of N,N-dimethylacrylamide-co-octafluoropentyl methacrylate-co-12-methacryloyloxydodecanoic acid.

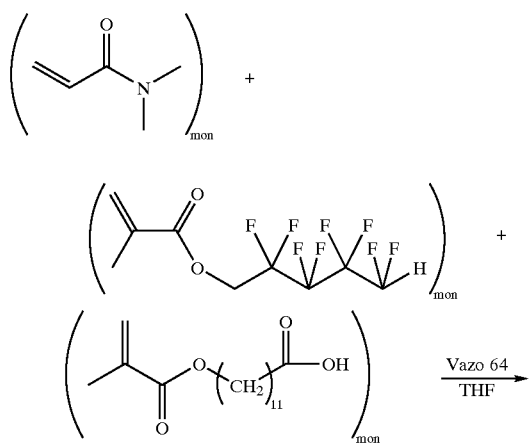

-continued

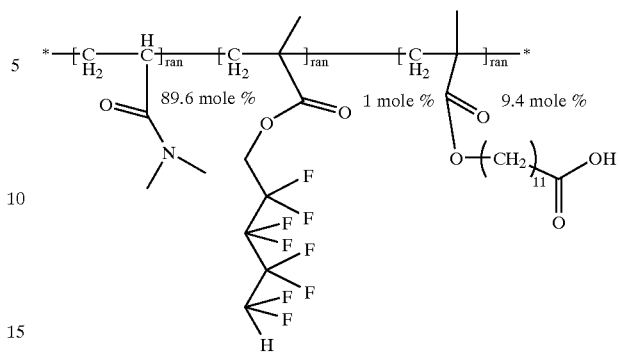

To a 500 ml reaction flask were added distilled N,N-dimethylacrylamide (DMA, 15 g, 0.151 moles), 1H,1H,5H-octafluoropentylmethacrylate (OFPMA 0.5 g, 0.0016 moles, used as received), 12-methacryloxydodecanoic acid (LMAA, 4.5 g, 0.0158 moles) Vazo 64 (AIBN, 0.032 g, 0.0002 moles) and anhydrous tetrahydrofuran (200 ml). The reaction vessel was fitted with a magnetic stirrer, condenser, thermal controller and a nitrogen inlet. Nitrogen was bubbled through the solution for 15 minutes to remove any dissolved oxygen. The reaction flask was then heated to 60° C. under a passive blanket of nitrogen for 72 hours. The reaction mixture was then added slowly to 2.5 L of heptane with good mechanical stirring. The reactive polymer precipitated and was collected by vacuum filtration. The solid was placed in a vacuum oven at 30° C. overnight to remove the ether leaving 18.7 g of reactive polymer (94% yield). The reactive polymer was placed in a desiccator for storage until use.

EXAMPLE 22

Example 22 illustrates the synthesis of a hydrophilic reactive polymer of N,N-dimethylacrylamide-co-laurylmethacrylate-co-glycidyl methacrylate.

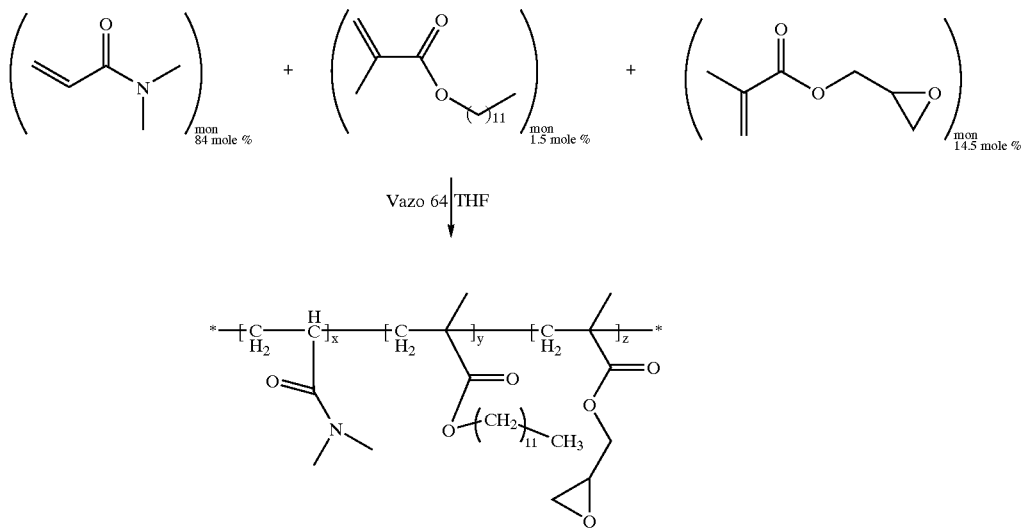

To a 1000 ml reaction flask were added distilled N,N-dimethylacrylamide (DMA,32 g, 0.32 moles), laurylmethacyy;ate (LMA, 1.5 g, 0.006 moles, used as received), distilled glycidyl methacrylate (GM, 8 g, 0.056 moles) Vazo-64 (AIBN, 0.06 g, 0.00036 moles) and tetrahydrofuran (600 ml). The reaction vessel was fitted with a magnetic stirrer, condenser, thermal controller and a nitrogen inlet. Nitrogen was bubbled through the solution for 15 minutes to remove any dissolved oxygen. The reaction flask was then heated to 60° C. under a passive blanket of nitrogen for 20 hours. The reaction mixture was then added slowly to 3 L of ethyl ether with good mechanical stirring. The reactive polymer precipitated and was collected by vacuum filtration. The solid was placed in a vacuum oven at 30° C. overnight to remove the ether leaving 29.2 g of reactive polymer (70% yield). The reactive polymer was placed in a desiccator for storage until use.

Many other modifications and variations of the present invention are possible in light of the teachings herein. It is therefore understood that, within the scope of the claims, the present invention can be practiced other than as herein specifically described.

What is claimed is:

1. A method for treating the surface of a medical device comprising:
   (a) forming a medical device from a material comprising monomeric units having reactive functionalities selected from the group consisting of azlactone, carboxylic acid, amine, hydroxy and epoxy functionalities, and combinations thereof;
   (b) forming a hydrophilic reactive polymer having complementary reactive functionalities along the polymer chain, said complementary reactive functionalities selected from the group consisting of azlactone, isocyanate, acid anhydride, epoxy, hydroxy, primary amine, secondary amine and carboxylic acid functionalities, and combinations thereof, wherein: when the hydrophilic reactive polymer comprises hydroxy or amine complementary reactive functionalities, the medical device monomeric units comprise azlactone reactive functionalities, or when the hydrophilic reactive polymer comprises carboxylic acid complementary functionality, the medical device monomeric units comprise epoxy reactive functionalities;
   (c) reacting the hydrophilic reactive polymer of (b) having complementary reactive functionalities along the polymer chain with said medical device monomeric unit reactive functionalities on or near the surface of the medical device of (a), thus forming a biocompatible surface on the medical device;
   (d) removing the biocompatible surface of step (c); and
   (e) repeating steps (b) and (c) to form a renewed biocompatible surface on said medical device having properties similar to the original biocompatible surface of step (c).

2. The method of claim 1, wherein the medical device is a silicone contact lens or intraocular lens and the hydrophilic reactive polymer is uncolored.

3. The method of claim 1, wherein the medical device is a silicone hydrogel, continuous-wear contact lens.

4. The method of claim 3 wherein said removing step (d) further comprises abrading said biocompatible surface with an abrasive particulate in an aqueous carrier solution.

5. The method of claim 4, wherein said abrasive particulate comprises silica or alumina.

6. The method of claim 1, wherein the hydrophilic reactive polymer comprises 1 to 100 mole percent of monomeric units having said reactive functionalities.

7. The method of claim 1, wherein the hydrophilic reactive polymer comprises 0 to 99 mole percent of monomeric units that are derived from non-reactive hydrophilic monomers.

8. The method of claim 1, wherein the polymer comprises 50 to 95 mole percent of monomeric units derived from non-reactive hydrophilic monomers selected from the group consisting of acrylamides, lactones, poly(alkylenepoxy) methacrylates, methacrylic acid or hydroxyalkyl methacrylates and 5 to 50 percent of monomeric units derived from functionally reactive monomers selected from the group consisting of epoxy, azlactone, and anhydride containing monomers.

9. The method of claim 1, wherein the medical device comprises a silicone hydrogel that is a polymerization product of a mixture comprising a silicon-containing monomer and a hydrophilic monomer.

10. The method of claim 1, wherein the hydrophilic reactive polymer comprises 0 to 35 mole percent monomeric units derived from hydrophobic monomers.

11. The method of claim 1, wherein the hydrophilic polymer comprises oxazolinone moieties having the following formula:

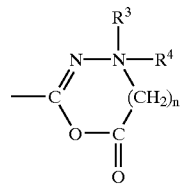

wherein $R^3$ and $R^4$ independently can be an alkyl group having 1 to 14 carbon atoms; a cycloalkyl group having 3 to 14 carbon atoms; an aryl group having 5 to 12 ring atoms; an arenyl group having 6 to 26 carbon atoms; and 0 to 3 heteroatoms selected from S, N, and nonperoxidic 0; or $R^3$ and $R^4$ taken together with the carbon to which they are joined can form a carbocyclic ring containing 4 to 12 ring atoms, and n is an integer 0 or 1.

12. The method of claim 11, wherein the polymer comprises the reaction product of a mixture of monomers comprising the monomer represented by the general formula:

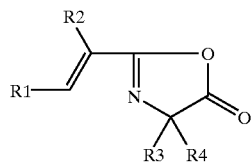

where $R^1$ and $R^2$ independently denote a hydrogen atom or a lower alkyl radical with one to six carbon atoms, and $R^3$ and $R^4$ independently denote alkyl radicals with one to six carbon atoms or a cycloalkyl radicals with 5 or 6 carbon atoms.

13. The method of claim 12, wherein the monomer is selected from the group consisting of 2-isopropenyl-4,4-dimethyl-2-oxazolin-5-one and 2-vinyl-4,4-dimethyl-2-oxazolin-5-one.

14. The method of claim 11, in the medical device is dipped in a solution comprising at least one hydrophilic reactive polymer in the absence of a coloring substance.

15. The method of claim 1 wherein said removing step (d) further comprises abrading said biocompatible surface.

16. The method of claim 1, wherein the medical device is a rigid contact lens.

17. The method of claim 16, wherein the rigid contact lens is a rigid-gas-permeable contact lens.

* * * * *

UNITED STATES PATENT AND TRADEMARK OFFICE
CERTIFICATE OF CORRECTION

PATENT NO.   : 6,599,559 B1                                          Page 1 of 1
DATED        : July 29, 2003
INVENTOR(S)  : Joseph A. McGee, Paul L. Valint, Jr. and James A. Bonafini, Jr.

It is certified that error appears in the above-identified patent and that said Letters Patent is hereby corrected as shown below:

<u>Column 38,</u>
Line 30, the chemical formula was replaced with the following:

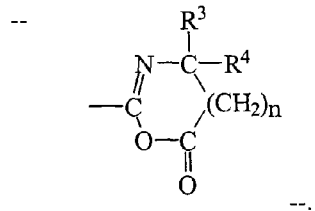

Signed and Sealed this

Seventeenth Day of February, 2004

JON W. DUDAS
*Acting Director of the United States Patent and Trademark Office*